United States Patent [19]
Veale et al.

[11] Patent Number: 6,054,593
[45] Date of Patent: Apr. 25, 2000

[54] PROLINE DERIVATIVES

[75] Inventors: Chris Allan Veale, Newark County, Del.; Peter Robert Bernstein, Wallingford, Pa.; Elwyn Peter Davies, Macclesfield, United Kingdom

[73] Assignee: Zeneca Limited, United Kingdom

[21] Appl. No.: 09/100,735

[22] Filed: Jun. 19, 1998

Related U.S. Application Data

[62] Division of application No. 08/918,626, Aug. 22, 1997, Pat. No. 5,808,097, which is a division of application No. 08/595,692, Feb. 2, 1996, Pat. No. 5,686,628.

[30] Foreign Application Priority Data

Feb. 3, 1995 [GB] United Kingdom .................. 9502152

[51] Int. Cl.$^7$ .................................................. C07D 207/16
[52] U.S. Cl. ............................................................. 548/537
[58] Field of Search ............................................. 548/537

[56] References Cited

U.S. PATENT DOCUMENTS

| | | |
|---|---|---|
| 4,277,395 | 7/1981 | Bey et al. . |
| 4,518,528 | 5/1985 | Rasnick . |
| 4,596,789 | 6/1986 | Dutta et al. . |
| 4,910,190 | 3/1990 | Bergeson et al. . |
| 5,055,450 | 10/1991 | Edwards et al. . |
| 5,194,588 | 3/1993 | Edwards et al. . |
| 5,414,132 | 5/1995 | Stein et al. . |
| 5,726,158 | 3/1998 | Edwards et al. . |

FOREIGN PATENT DOCUMENTS

| | | |
|---|---|---|
| 195212 | 9/1986 | European Pat. Off. . |
| 2171103 | 8/1986 | United Kingdom . |

OTHER PUBLICATIONS

Imperiali, B. & Abeles, R. H. *Biochemistry* (1986), 25, 3760–3767 (including twenty (20) pages of supp. material).
Imperiali, B. & Abeles, R. H. *Tetrahedron Lett.* (1986), 27, 135–138.
*Chem. Abst.* vol. 92, (1980), 175119.
*Chem. Abst.* vol. 102, (1985), 84468.
Gelb, M. H., Svaren, J.P., & Abeles, R. H. *Biochemistry* (1985), 24, 1813–1817.
Prestwich, G. D., et al. *Archives of Biochemistry and Biophysics* (1984), 228, 639–645.
Abdel–Aal, et al. *Pesticide Biochemistry and Physiology* (1984), 21, 232–241.
Hammock, B. D., et al. *Pesticide Biochemistry and Physiology* (1982), 17 , 76–88.
Brodbeck, U., et al. *Biochimica et Biophysica Acta* (1979), 567, 357–369.
Kingsbury, C. A., et al. *J. Chem. Soc. Perkin Trans. II* (1982), 867.
McBee, E. T., et al. *J. Amer. Chem. Soc.* (1956), 78, 4053.
Cook, D. J., et al. *J. Amer. Chem. Soc.* (1954), 76, 83.
Powers et al. *Biochimica et Biophysica Acta* (1977), 485: 156–166.
*Chemical Abstracts*, vol. 99, No. 21, Nov. 21 1983, p. 547, Abstract No. 174904g, Columbus, Ohio, US; D.B. Dess et al.; "Readily accessible 12–I–5 oxidant for the conversion of primary and secondary alcohols to aldehydes and ketones" J. Org. Chem. 1983, 48(22), 4155–6.
Rich, D. H., et al., *Biochem. Biophys. Res. Comm.* 1982 104(2), 1127–1133.
Hori, H., et al., Proc. 9th American Peptide Symposium, Toronto, Jun. 1985, pp. 819–922.
Thaisrivongs, S., *J. Med. Chem.*, 1985, 28, 1553–1555.
Edwards, P.D. (1992) (Tetrahedron Letters 33(30):4279–4282.

*Primary Examiner*—Robert W. Ramsuer
*Assistant Examiner*—Ebenezer Sackey
*Attorney, Agent, or Firm*—Richard V. Person

[57] ABSTRACT

The present invention relates to particular forms of a novel 1-substituted-N-[2-methyl-1-(trifluoroacetyl)propyl] pyrrolidine-2-carboxamide which are inhibitors of human leukocyte elastase (HLE), also known as human neutrophil elastase (HNE), making them useful whenever such inhibition is desired, such as for research tools in pharmacological, diagnostic and related studies and in the treatment of diseases in mammals in which HLE is implicated. The invention also includes pharmaceutical compositions containing such forms, processes for preparing the forms and intermediates useful in the synthesis of the forms.

2 Claims, 8 Drawing Sheets

PROLINE DERIVATIVES

This is a division of application Ser. No. 08/918,626 filed on Aug. 22, 1997, now U.S. Pat. No. 5,808,097 which in turn is a division of application Ser. No. 08/595,692 filed Feb. 2, 1996 now U.S. Pat. No. 5,686,628 issued Nov. 11, 1997.

The present invention relates to novel proline derivatives, and more particularly to particular forms of a novel 1-substituted-N-[2-methyl-1-(trifluoroacetyl)propyl] pyrrolidine-2carboxamide derivative which are inhibitors of human leukocyte elastase (HLE), also known as human neutrophil elastase (HNE), which are of value, for example, as a research tool in pharmacological, diagnostic and related studies and in the treatment of diseases in mammals in which HLE is implicated. For example, HLE has been implicated causally in the pathogenesis of acute respiratory distress syndrome (ARDS), rheumatoid arthritis, atherosclerosis, pulmonary emphysema, and other inflammatory disorders, including airway inflammatory diseases characterized by increased and abnormal airway secretion such as acute and chronic bronchitis and cystic fibrosis. Also, HLE has been causally implicated in certain vascular diseases and related conditions (and their therapy) in which neutrophil participation is involved or implicated, for example, in hemorrhage associated with acute non-lymphocytic leukemia, as well as in reperfusion injury associated with, for example, myocardial ischaemia and related conditions associated with coronary artery disease such as angina and infarction, cerebrovascular ischaemia such as transient ischaemic attack and stroke, peripheral occlusive vascular disease such as intermittent claudication and critical limb ischaemia, venous insufficiency such as venous hypertension, varicose veins and venous ulceration, as well as impaired reperfusion states such as those associated with reconstructive vascular surgery, thrombolysis and angioplasty. The invention also concerns methods of treating one or more of these disease conditions and the use of one or more of the particular forms of the novel dervative in the manufacture of a medicament for use in one or more of said conditions. The invention further concerns pharmaceutical compositions containing one or more of the particular forms of the novel derivative as active ingredient, as well as processes for the manufacture of the particular forms of the novel derivative, novel intermediates useful in said processes and methods for the preparation of said intermediates.

Because of HLE's apparent role, there has been considerable research effort in recent years towards the development of HLE inhibitors. In U.S. Pat. No. 4,910,190 is disclosed a series of structurally related peptidoyl trifluoromethane derivatives which are HLE inhibitors. We have now discovered that particular forms of the novel 1-substituted-N-[2-methyl-1-(trifluoroacetyl)-propyl]-pyrrolidine-2-carboxamide derivative of formula I (set out hereinafter) are unexpectedly potent inhibitors of HLE.

Figure 1:
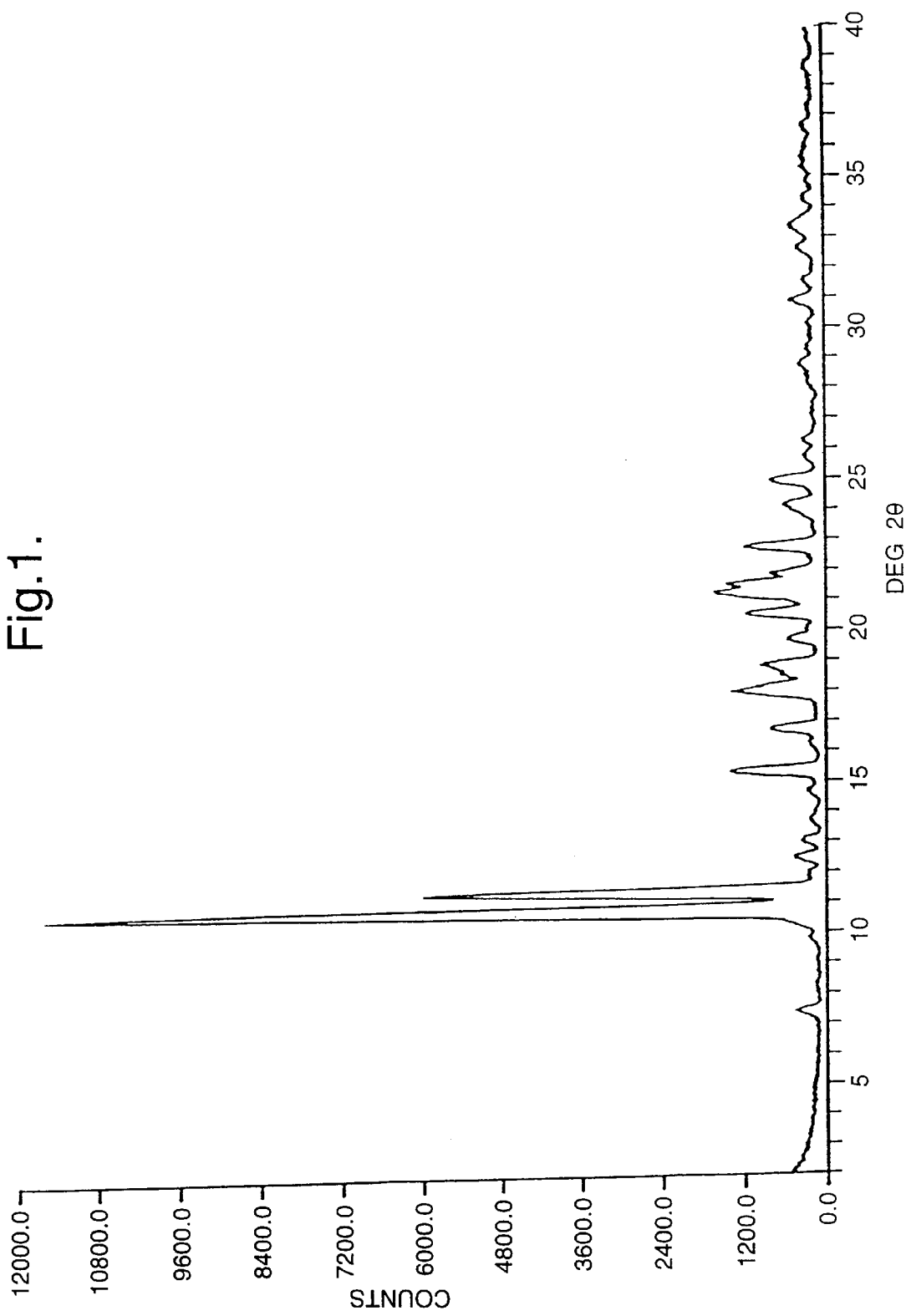
FIG. 1 shows the X-ray powder diffraction spectrum of a typical sample of the crystalline form of the SSS diastereoisomer of formula I, when substantially or essentially pure and in hydrated form, referred to as Form A.

According to one aspect of the invention, there is provided the compound (S)-1-[(S)-2-(methoxycarbonylamino)-3-methylbutyryl]-N-[2-methyl-1-(trifluoroacetyl)propyl] propyl or a solvate thereof, both in the form of a diastereomeric mixture of (S)-1-[(S)-2-(methoxycarbonylamino)-3-methylbutyryl]-N-[(S)-2-methyl-1-(trifluoroacetyl)propyl]pyrrolidine-2-carboxamide (or a solvate thereof) and (S)-1-[(S)-2-(methoxycarbonylamino)-3-methylbutyryl]-N-[(R)-2-methyl-1-(trifluoroacetyl)propyl]pyrrolidine-2-carboxamide (or a solvate thereof) and in the form of the substantially or essentially pure diastereoisomer (S)-1-[(S)-2-(methoxycarbonylamino)-3-methylbutyryl]-N-[(S)-2-methyl-1-(trifluoroacetyl)propyl]pyrrolidine-2-carboxamide or a solvate thereof.

It will be appreciated that the compound of formula I has three chiral centers (identified by * and # in formula I) and can therefore exist in eight different stereomeric forms, or as a diastereomeric mixture of two or more of these forms. For example, the compound (S)-1-[(S)-2-(methoxycarbonylamino)-3-methylbutyryl]-N-[2-methyl-1-(trifluoroacetyl)propyl]pyrrolidine-2-carboxamide is a compound of the formula I in which the two chiral centers identified by * have the S configuration and the third chiral center identified by # has the RS configuration. The compound is therefore a diastereomeric mixture comprising the diastereoisomer with the chiral centers marked * and # all having the S configuration, that is (S)-1-[(S)-2-(methoxycarbonylamino)-3-methylbutyryl]-N-[(S)-2-methyl-1-(trifluoroacetyl)propyl]pyrrolidine-2-carboxamide (hereinafter referred to as the "SSS diastereoisomer" of formula I and which may also be represented as shown in formula Ia in which a thickened bond denotes a bond projecting from the plane of the paper) and the diastereoisomer with the chiral centers marked * having the S configuration and that marked # having the R configuration, that is (S)-1-[(S)-2-(methoxycarbonylamino)-3-methylbutyryl]-N-[(R)-2-methyl-1-(trifluoroacetyl)propyl]pyrrolidine-2-carboxamide (hereinafter referred to as the "SSR diastereoisomer" of formula I), or solvates thereof. Such a diastereomeric mixture includes, for example, a mixture containing approximately equal amounts of the SSS and SSR diastereoisomers, i.e. the SSS:SSR ratio is about 1:1. For example, diastereomeric mixtures comprising SSS and SSR diastereoisomers in ratios of 53:47 and 47:53 (SSS:SSR) have been obtained. Particular forms of the compound of formula I which are preferred are diastereomeric mixtures which are enriched in the SSS diastereoisomer, i.e. the ratio of SSS:SSR is greater than 1:1. An especially preferred form of the compound is substantially or essentially pure SSS diastereoisomer, that is SSS diastereoisomer containing less than 5% (more particularly less than 3% and preferably less than 2%) of other diastereoisomers.

It will be appreciated that the SSS diastereoisomer of formula I may also form a diastereomeric mixture with one or more other forms of formula I, for example (S)-1-[2-methoxycarbonylamino-3-methylbutyryl]-N-[(S)-2-methyl-1-(trifluoroacetyl)propyl]pyrrolidine-2-carboxamide (a diastereomeric mixture of the SSS and RSS forms of formula I) or 1-[(S)-2-methoxycarbonylamino-3-methylbutyryl]-N-[(S)-2-methyl-1-(trifluoroacetyl)propyl]pyrrolidine-2-carboxamide (a diastereomeric mixture of the SSS and SRS forms of formula I) may be obtained. These particular diastereomeric mixtures, and other diastereomeric mixtures containing about 50% or more of the SSS diastereoisomer together with one or more other possible diastereoisomers with different configurations at the chiral centers marked by * and # in formula I are therefore further aspects of the present invention.

A diastereomeric mixture of the SSS and SSR diastereoisomers may exist in an amorphous, non-crystalline form or in a crystalline form, dependent on the ratio of SSS:SSR diastereoisomers present. A preferred diastereomeric mixture is one which can be isolated in crystalline form, which is particularly advantageous in the manufacture of the compound, or formulations thereof, to the purity levels and uniformity required for regulatory approval. It will be appreciated that it is extremely difficult to obtain a compound which is a single diastereoisomer completely free of the other possible diastereomeric forms, particularly a compound which has three chiral centers. The present invention therefore includes a crystalline form of the SSS diastereoisomer of formula I, or solvate thereof, which contains other possible diastereoisomers with different configurations at the chiral centers indicated by * and # in formula I. It has been found that a crystalline diastereomeric mixture of the SSS and SSR diastereoisomers or a hydrate thereof, can be obtained which is substantially or essentially a diastereomeric mixture of SSS and SSR diastereoisomers in a ratio (SSS:SSR) of 65:35 or greater, i.e. it contains 35% or less of the SSR diastereoisomer. The present invention therefore includes a crystalline form of the compound of formula I, or a solvate thereof, with a content of at least 65% of the SSS diastereoisomer. Preferably the crystalline diastereomeric mixture has, for example, a ratio of SSS:SSR which is 80:20 or greater, for example 95:5 or greater, and especially 98.5:1.5 or greater. An especially preferred form of the compound of the invention is crystalline SSS diastereoisomer which is substantially or essentially pure, i.e. it contains less than 5% of other diastereoisomers, for example less than 5% of the SSR diastereoisomer, preferably less than 3% of the SSR diastereoisomer, and more preferably less than 2% of the SSR diastereoisomer.

An amorphous or crystalline diastereomeric mixture of SSS and SSR forms, or substantially or essentially pure SSS diastereoisomer, exist in a form which is substantially or essentially free of solvent (hereinafter referred to as the "ketone" form and as illustrated in Formula Ia for the pure SSS diastereoisomer), or as a solvated, for example, hydrated form, or as a mixture of the ketone and solvated (hydrated) forms. The hydrated form may exist, for example, as a gem-diol of the trifluoroketone functionality, that is as a compound of the formula Ib (set out hereinafter) for substantially or essentially pure SSS diastereoisomer, or as a compound of the formula Ic (set out hereinafter), or as a form which incorporates a water molecule as part of the crystal lattice, or mixtures of such forms. The compounds of formula Ib or Ic may, for example, be further hydrated.

It will be appreciated that the degree of hydration of a diastereomeric mixture or substantially or essentially pure SSS diastereoisomer may be expressed as a ratio of hydrate to ketone forms. For example, an amorphous, non-crystalline diastereomeric mixture of SSS and SSR forms has been isolated in which the ratio of hydrated form to ketone form varies, for example, from about 30:70 (i.e. enriched in the ketone form) to about 95:5 or greater (i.e. substantially or essentially in the hydrated form), including such ratios as about 50:50 and about 60:40. Crystalline forms have, for example, been obtained which have an SSS:SSR ratio of about 95:5 together with a hydrate:ketone ratio of about 80:20 and which have an SSS:SSR ratio of about 65:35 or greater (such as 98.5:1.5) and are substantially or essentially in the hydrated form. Crystalline hydrates of substantially or essentially pure SSS diastereoisomer containing approximately 4.1% (w/w) and 7.8% (w/w) of water have also been obtained. Such particular forms are further aspects of the invention. It is to be further understood that the present invention also encompasses any ketal or hemiketal (or mixture thereof) of a diastereomeric mixture or of a form of the SSS diastereoisomer, or of a solvate thereof, referred to herein which is converted to the gem-diol in vivo, for example by hydrolysis or enzymatic cleavage (and wherein the residue is pharmaceutically acceptable). The present invention also includes any tautomer or pro-drug of the SSS diastereoisomer or a solvate thereof.

It will be appreciated that the compound of formula Ib may be referred to as the gem-diol form of the compound of formula Ia or by the chemical name (S)-1-[(S)-2-(methoxycarbonylamino)-3-methylbutyryl)-N-[(S)-2-methyl-1-(2,2,2-trifluoro-1,1-dihydroxyethyl)-propyl]pyrrolidine-2-carboxamide. It will also be appreciated that an alternative name for the compound of formula Ia is methyl N-[(1S)-1-((2S)-2-[N-((1S)-2-methyl1-(2,2,2-trifluoroacetyl)propyl)-carbamoyl]pyrrolidine-1-ylcarbonyl)-2-methylpropyl]carbamate and an alternative name for the compound of formula Ib is methyl N-[((S)-1-((2S)-2-[N-((S)-3,3,3-trifluoro-2,2-dihydroxy-1-isopropylpropyl)carbamoylpyrrolidin-1-yl-carbonyl)-2-methylpropyl]-carbamate.

The melting point of crystalline SSS diastereoisomer containing SSR diastereoisomer generally depends on the level of SSR diastereoisomer present and the level of solvation (hydration). It may be determined by conventional procedures well known in the art, for example, by differential scanning calorimetry (DSC).

Preferably the crystalline SSS diastereoisomer is in a hydrated form. For example, hydrated forms of the SSS diastereoisomer have been found which have an advantageous property that they are non-hygroscopic, for example Form A and Form B referred to hereinafter. Thus a preferred form of the SSS diastereoisomer is a crystalline form containing less than 5% (preferably less than 3% and especially less than 2%) of the SSR diastereoisomer and substantially or essentially in a hydrated form. Such crystalline hydrated forms, for example Form A and Form B, have been found to possess good bioavailability and good solubility in aqueous buffer, which are both advantageous properties.

Figure 2:
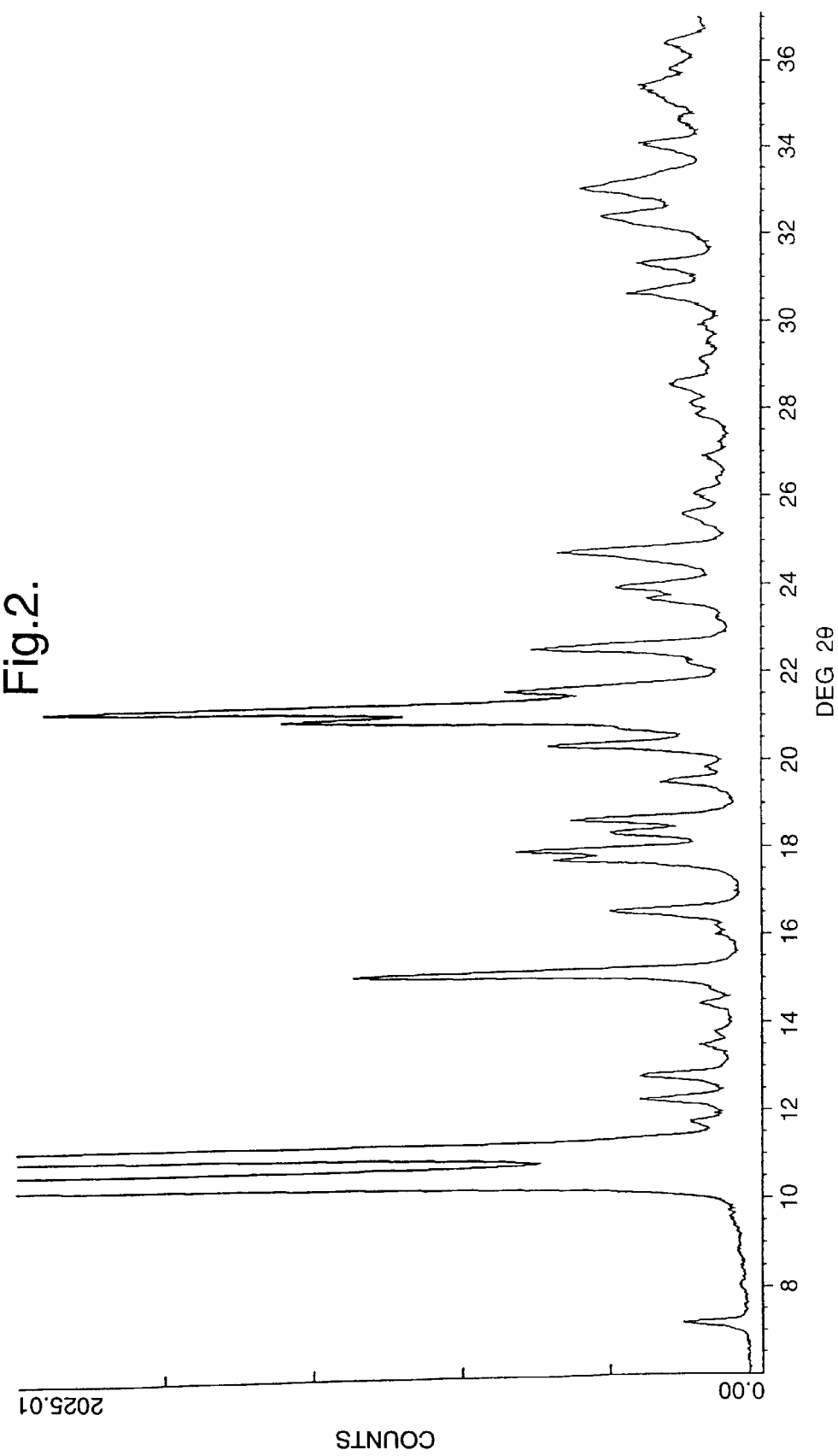
FIG. 2 shows the X-ray powder diffraction spectrum of FIG. 1 on an expanded scale.

A particularly preferred crystalline form of the SSS diastereoisomer of formula I, when it is substantially or essentially pure and in a hydrated form, has an X-ray powder diffraction pattern including two major specific peaks at about 2θ=10.8 and 11.4°. This form (herein referred to as Form A) contains approximately 4.1% water. The X-ray powder diffraction pattern also includes less relatively intense specific peaks occurring at about 2θ=15.4, 16.8, 18.2, 18.6, 20.6, 21.6, 21.9, 22.8 and 25.0°. The X-ray powder diffraction spectrum (XDS) of a typical sample of this form is shown in FIGS. 1 and 2 hereinafter, where FIG. 2 shows the less intense peaks on an expanded scale. Further physical data suggests that this crystalline form is substantially or essentially in the form of the diol of formula Ib.

Figure 3:
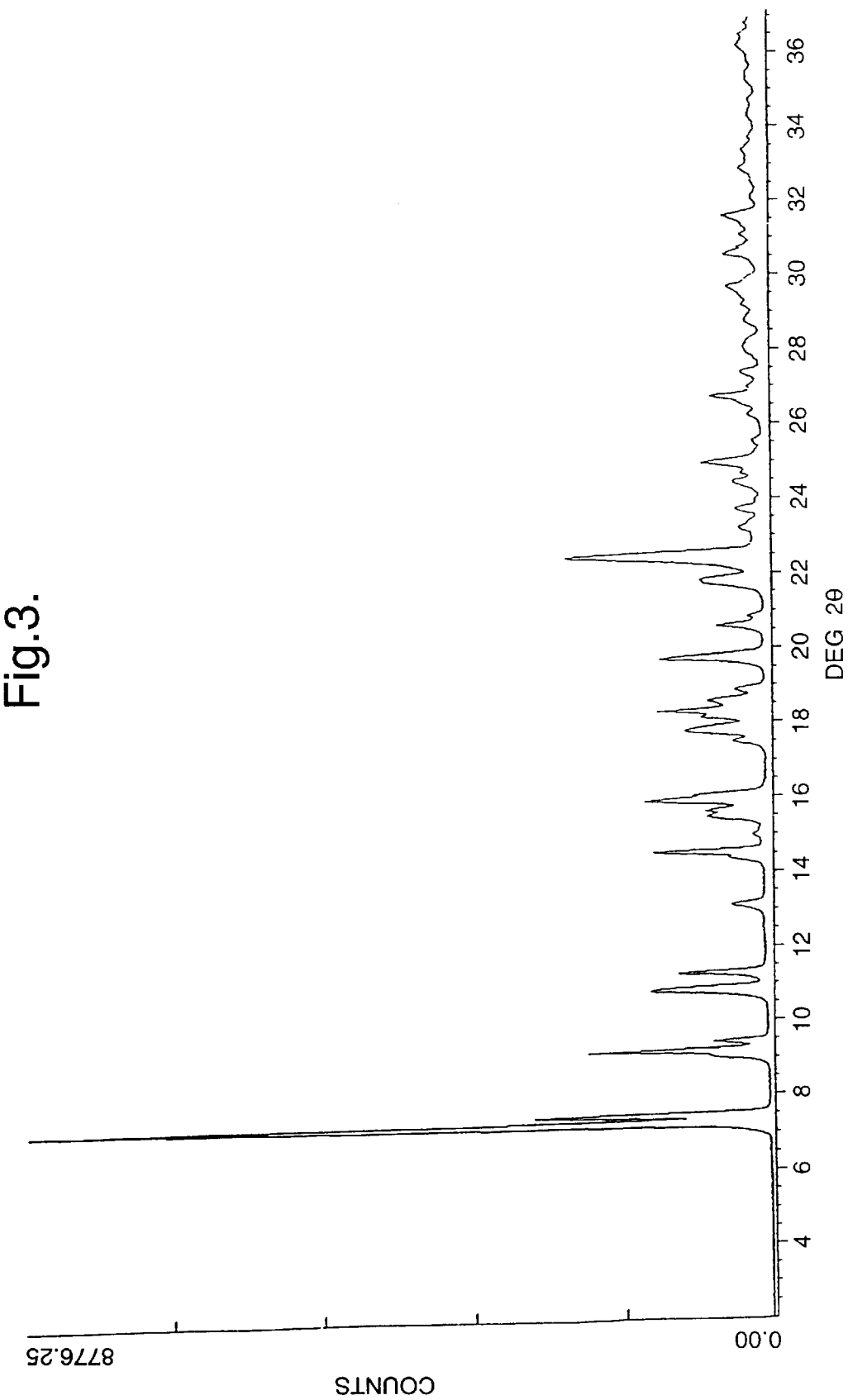
FIG. 3 shows the X-ray powder diffraction spectrum of a typical sample of the crystalline form of the SSS diastereoisomer of formula I, when substantially or essentially pure and in hydrated form, referred to as Form B.

A further preferred crystalline form of the SSS diastereoisomer of formula I, when it is substantially or essentially pure and in a hydrated form, has an X-ray powder diffraction pattern including a major specific peak at about 2θ=7.2°. This form (herein referred to as Form B) contains approximately 7.8% w/w (for example 7.3–8.3% w/w) of water. The X-ray powder diffraction pattern also includes less relatively intense specific peaks occurring at about 2θ=7.4, 9.0, 10.8, 11.3, 14.5, 15.9, 17.8, 18.1, 19.7 and 22.5°. The XDS of a typical sample of this form is shown in FIG. 3 hereinafter. Further physical data suggests that this crystalline form is substantially or essentially the monohydrate of the diol of formula Ib.

Figure 4:
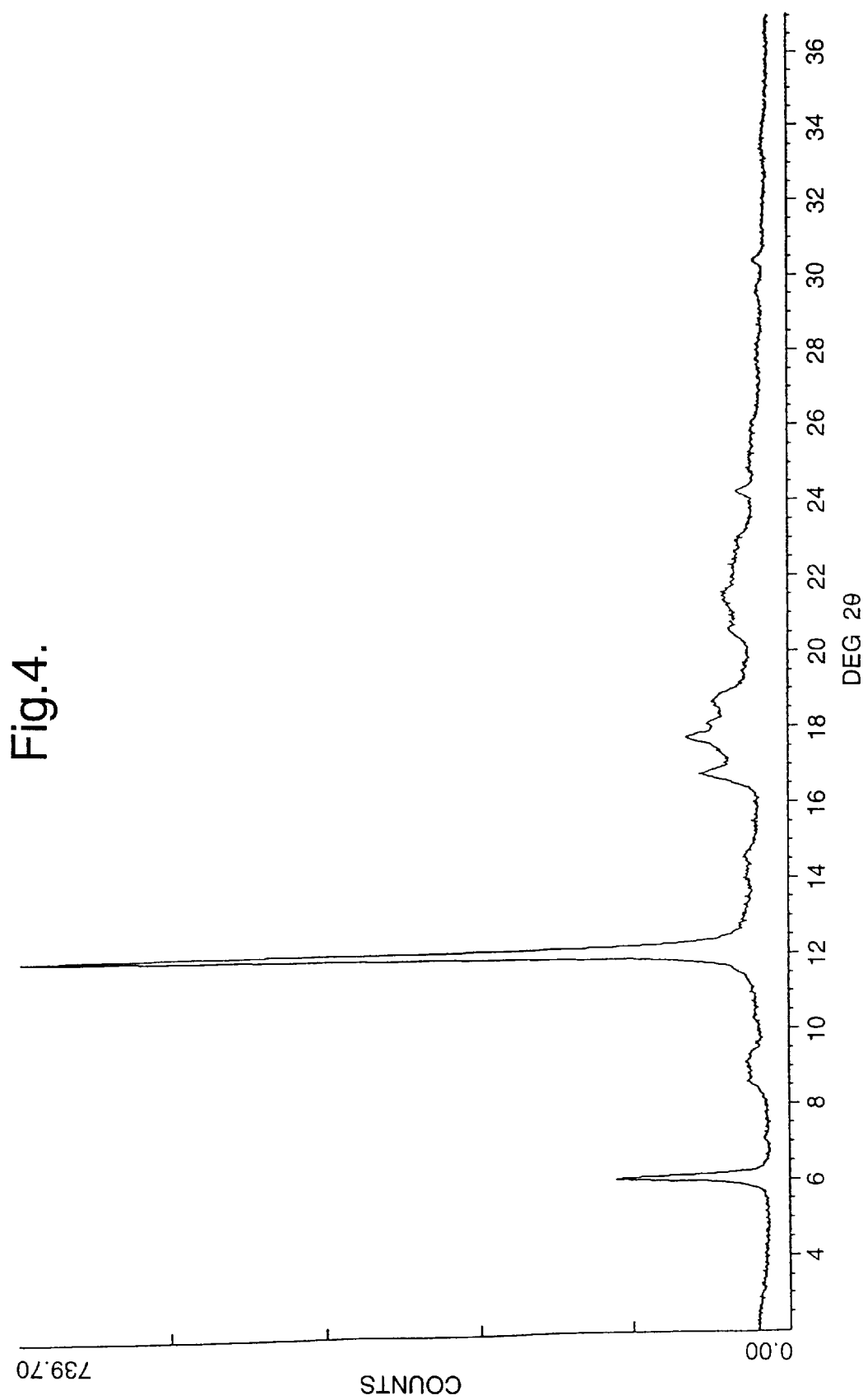
FIG. 4 shows the X-ray powder diffraction spectrum of a typical sample of the SSS diastereoisomer of formula I in the "ketone" form.

When it is substantially or essentially pure and substantially or essentially free of solvent (i.e. in the "ketone" form), the SSS diastereoisomer has an X-ray powder diffraction pattern including a major specific peak at about 2θ=12.1. This pattern also includes less relatively intense peaks occurring at about 2θ=6.0, 16.8 and 17.7°. The XDS of a typical sample of the "ketone" form is shown in FIG. 4 hereinafter.

The X-ray powder diffraction spectra were determined, for example, using Scintag XDS-2000 X-ray diffractometer, with an EC&G solid-state photon detector, GLP Series (germanium) operated by a Hicrovax computer and using the Diffraction Management System software supplied by Scintag Inc., Sunnydale, Calif., USA. The X-ray tube used was a Cu K-alpha with a wavelength of 1.5406A at 45 KV and 40 mA. The receiving slits were set at 2 and 4 mm and the diverging slits set at 0.5 and 0.2 mm with respect to the path of the incident beam. The spectra were obtained in the continuous scan mode with a chopper increment of 0.02. Each sample was exposed at 1 degree 2-theta per minute (running time was 38 minutes) and collected from 2 to 40 degrees 2-theta, to produce a trace of spacings against intensity for this range.

For diffraction analysis the samples were packed into round aluminium alloy sample pans with a diameter of 25 mm and depth of 2 mm. The powder sample was placed in the pan so that an amount in excess of the pan volume was present and subsequently leveled to the pan rim with a glass microscope slide. Silicon type-NBS 640b was used as an external standard.

Alternatively a Siemens D5000 X-ray diffractometer was used, recording the diffractogram in θ—θ mode over the range 2 to 40 degrees 2-theta with 4 seconds exposure per 0.02° 2θ increment.

Figure 5:
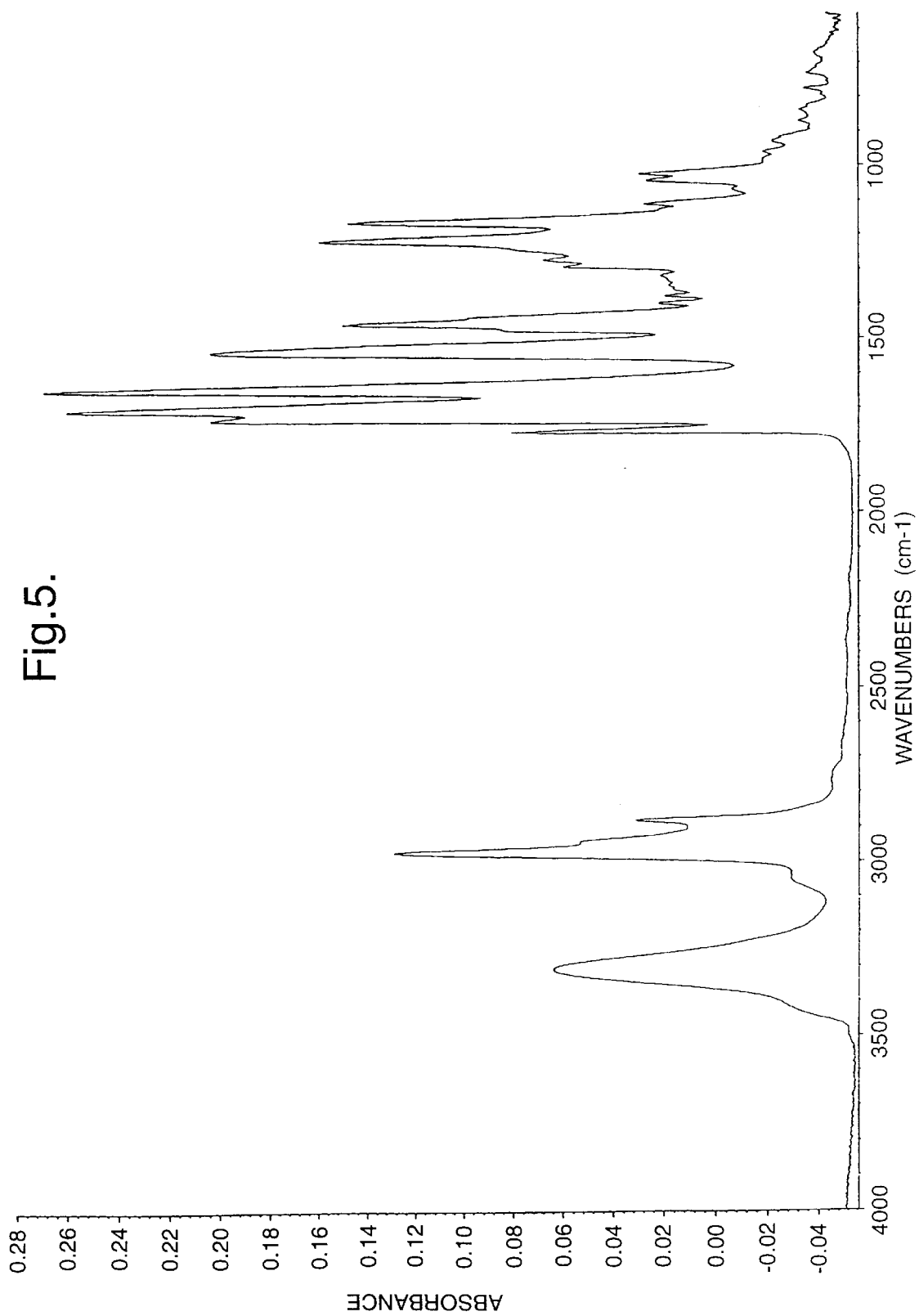
FIG. 5 shows the infra-red spectrum of a typical sample of the crystalline form of the SSS diastereoisomer of formula I referred to as Form A.

An infra-red spectrum was obtained for a typical sample of Form A. The infra-red spectrum was obtained by the solvent cast technique well known in the art, from acetonitrile castings of a sample onto a salt window for analysis by direct transmission. The infra-red spectrum was determined over the wave number range 4000 to 400 $cm^{-1}$. The infra-red spectrum is shown in FIG. 5. The spectrum of FIG. 5 includes sharp peaks at about 2968, 1762, 1721, 1690, 1632, 1525, 1447, 1207 and 1154 $cm^{-1}$.

Figure 6:
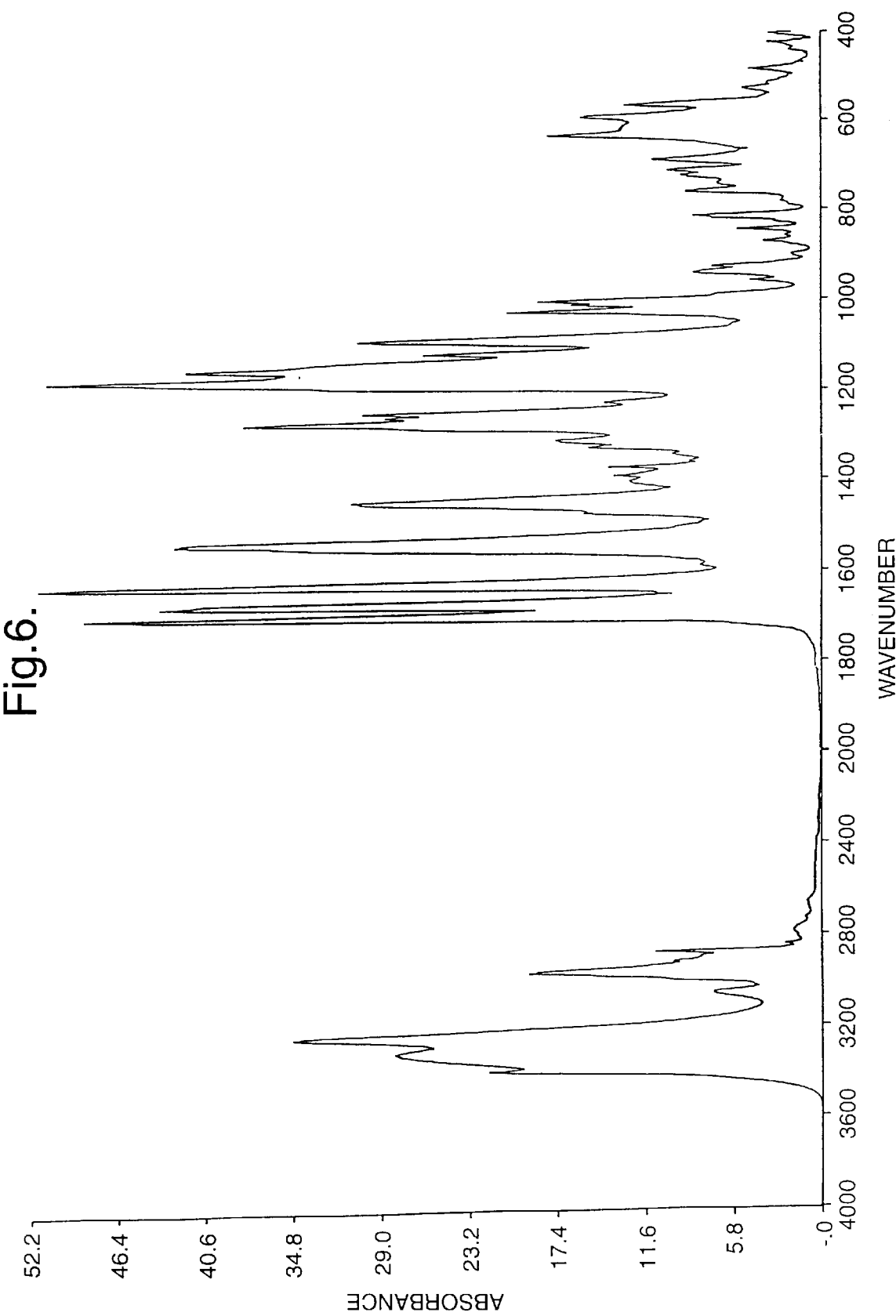
FIG. 6 shows the infra-red spectrum of a typical sample of the crystalline form of the SSS diastereoisomer of formula I referred to as Form A obtained using a 2% dispersion of the sample in potassium bromide.
Figure 7:
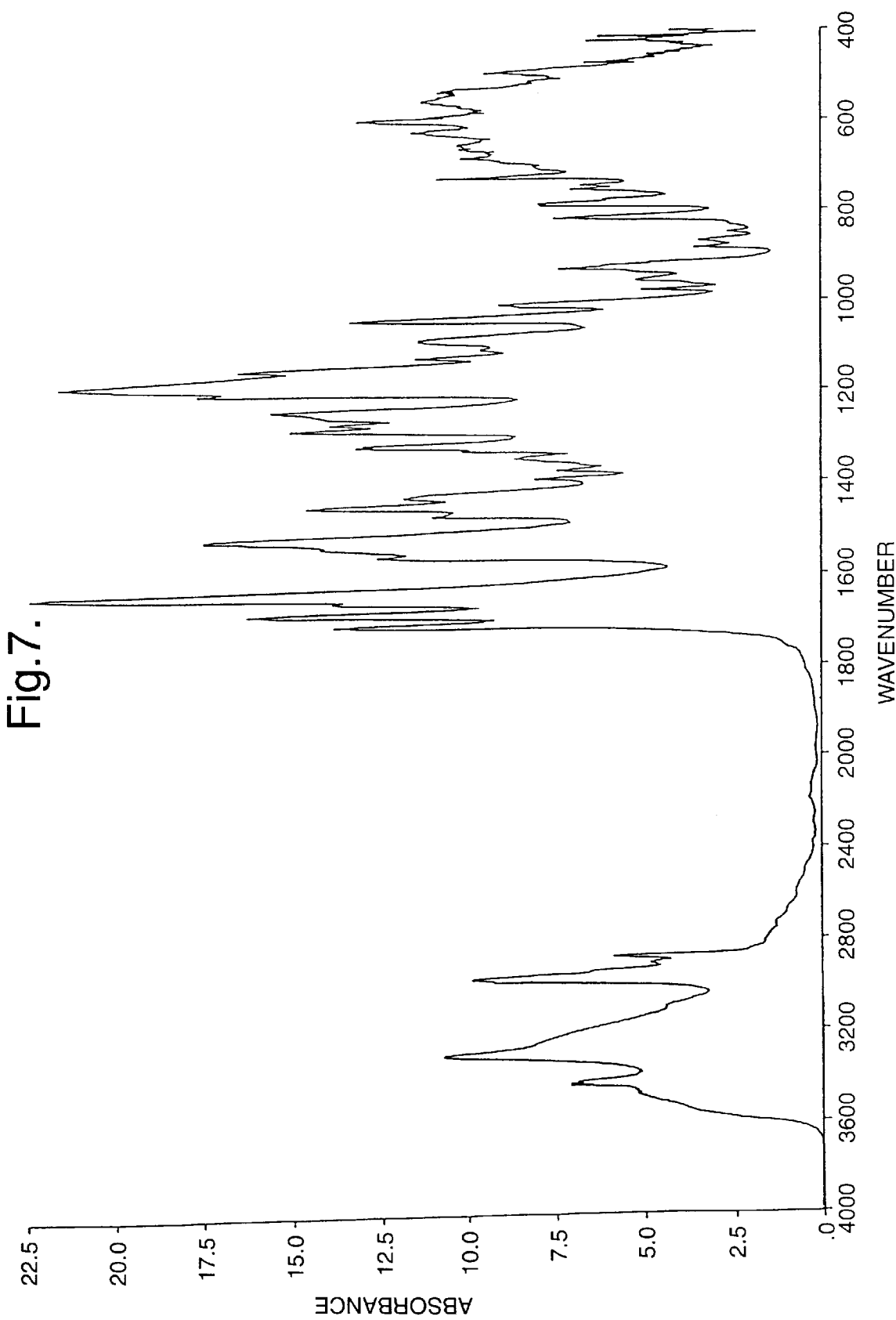
FIG. 7 shows the infra-red spectrum of a typical sample of the crystalline form of the SSS diastereoisomer of formula I referred to as Form B obtained using conditions similar to the conditions used for FIG. 6.
Figure 8:
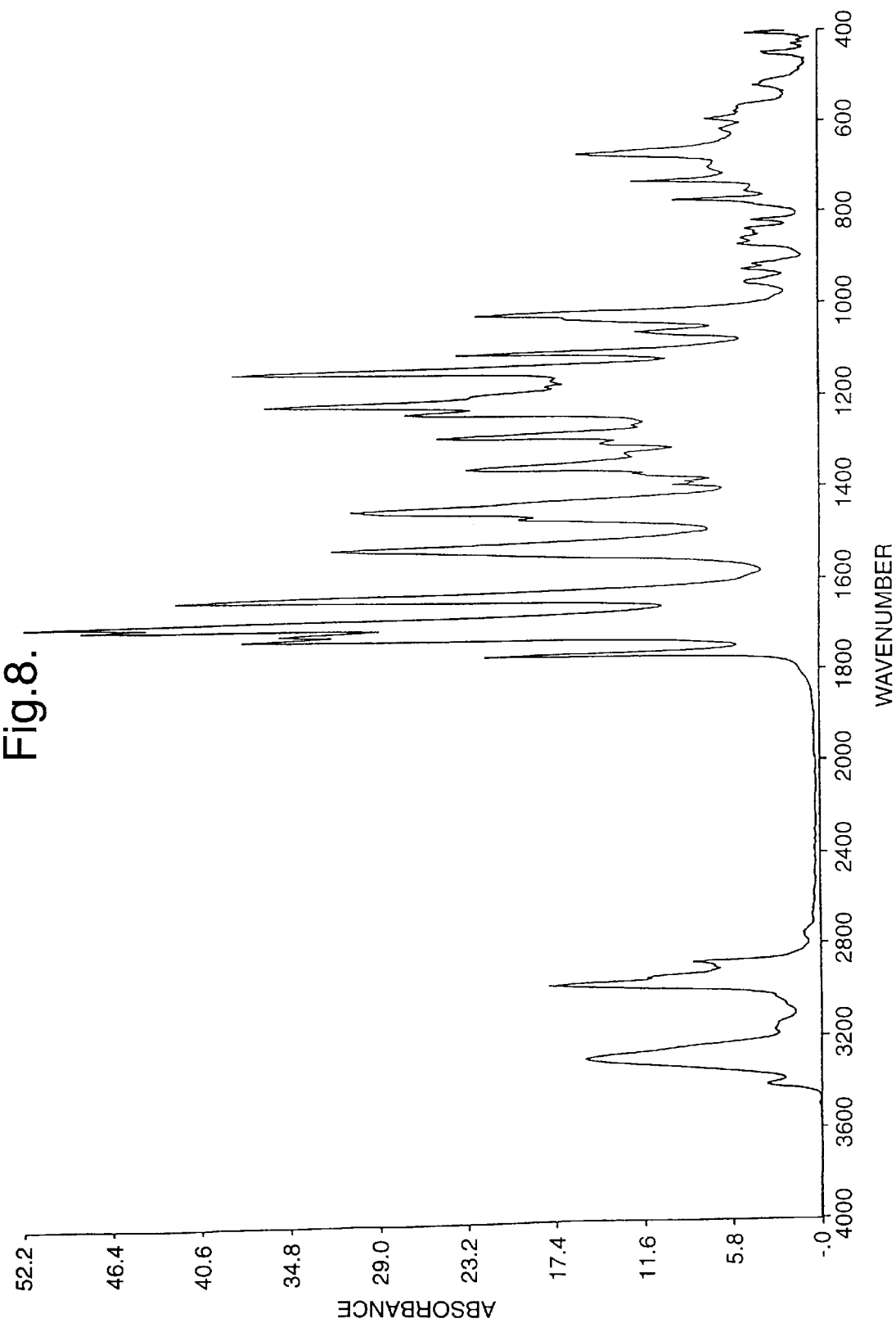
FIG. 8 shows the infra-red spectrum of a typical sample of the SSS diastereoisomer of formula I in substantially the "ketone" form obtained using conditions similar to the conditions used for FIG. 6.

The infra-red spectrum was also obtained for a typical sample of Form A using a Nicolet 20SXC FTIR spectrometer. The spectrum was obtained using a 2% dispersion of the sample in potassium bromide. The infra-red spectrum is shown in FIG. 6 hereinafter. The spectrum of FIG. 6 includes sharp peaks at about 3402, 3321, 3252, 3060, 2967, 2878, 1699, 1674, 1629, 1535, 1532, 1446, 1271, 1258, 1249, 1175, 1152, 1118, 1089, 1029, 1013, 1004, 635, 593 and 567 $cm^{-1}$. Using similiar conditions, an infra-red spectrum was obtained for a typical sample of Form B. The infra-red spectrum is shown in FIG. 7 hereinafter. The spectrum of FIG. 7 includes sharp peaks at about 3428, 3304, 2971, 2875, 1708, 1682, 1637, 1556, 1518, 1470, 1449, 1428, 1316, 1310, 1277, 1265, 1236, 1196, 1175, 1144, 1120, 1081, 1036, 1005, 928, 818, 790 and 727 $cm^{-1}$. Using similar conditions, an infra-red spectrum was obtained for a typical sample of the SSS diastereoisomer in substantially the "Ketone" form. The infra-red spectrum is shown in FIG. 8. The spectrum of FIG. 8 includes sharp peaks at about 3415, 3300, 2967, 2876, 1764, 1723, 1711, 1695, 1686, 1634, 1527, 1445, 1356, 1286, 1234, 1213, 1139, 1105, 1061, 1020, 774, 732 and 671 $cm^{-1}$.

It will be understood that the 2θ values of the X-ray powder diffraction patterns and the wavelengths of the infra-red spectra may vary slightly from one machine to another and so the values quoted are not to be construed as absolute. For example, the two major specific peaks which occurred at about 2θ=10.8 and 11.4° for a typical sample of Form A when a Scintag XDS-2000 X-ray diffractometer was used, occurred at about 2θ=10.6 and 11.2° respectively when a Siemens D5000 X-ray diffractometer was used (with the less intense peaks also occurring at a proportionately lower relative 2θ value).

It will be appreciated that the hydrogen atoms of the hydroxyl groups of the forms of formula Ib or Ic (or a hydrate thereof) are acidic and that such compounds may therefore form crystalline pharmaceutically-acceptable salts, using conventional procedures, for example with bases affording physiologically-acceptable cations, for example alkali metal (such as sodium or potassium), alkali earth metal or organic amine salts. The invention therefore includes crystalline pharmaceutically-acceptable salts of the forms of formula Ib and Ic or a hydrate thereof.

The various forms of the compound of formula I referred to above, or solvates (hydrates) thereof, may be obtained, for example, by the following processes, which are further separate aspects of the invention.

A non-crystalline (amorphous) diastereomeric mixture of SSS and SSR diastereoisomers may be obtained by oxidation of the compound of formula II with a suitable oxidising agent.

A suitable oxidising agent is one known in the art for the conversion of a hydroxy group into a ketone group. Suitable oxidising agents and conditions include, for example, the use of oxalyl chloride, dimethyl sulfoxide, and a tertiary amine; the use of acetic anhydride and dimethyl sulfoxide; the use of chromium trioxide pyridine complex in dichloromethane; the use of hypervalent iodine reagent, such as 1,1,1-triacetoxy-2,1-benzoxidol-3(3H)-one with trifluoroacetic acid in dichloromethane; the use of excess dimethylsulphoxide and a water soluble carbodiimide in the presence of dichloroacetic acid; or an alkaline aqueous alkali metal permanganate, such as alkaline aqueous potassium permanganate or sodium permanganate solution. Particularly suitable oxidising agents are the latter two named, especially alkaline aqueous potassium or sodium permanganate solution, for example a mixture of sodium hydroxide and potassium or sodium permanganate.

The compound of formula II may be obtained, for example, as shown in Schemes 1 and 2, using conventional procedures, or as illustrated in the Examples. Steps (a) to (d) of Scheme 1 may be carried out as described in U.S. Pat. No. 5,194,588 or European Patent 189305. Step (e) is carried out using conventional procedures for the formation of a carbamate from a primary amine, for example using a methyl halogenoformate, such as methyl chloroformate, in the presence of a suitable base such as triethylamine or N-methylmorpholine, and in a suitable solvent or diluent, for example a chlorinated hydrocarbon (such as dichloromethane or chloroform) or an ethereal solvent (such as tetrahydrofuran or dioxan), and at a temperature in the range of, for example, −10° C. to 50° C., such as 0° C. to 30° C. The reaction steps of Scheme 2 include conventional steps of protection (step (10)), deprotection or selective deprotection (steps (1), (3), (6), (8), (9) and (12)), coupling (steps (4), (5), (13) and (14) and carbamate formation (steps (2), (7) and (11)) well known in the art.

It will be appreciated that diastereomeric mixtures of SSS and RSS diastereoisomers and of SSS and SRS diastereoisomers may be obtained using analogous procedures, with appropriate choice of L- or DL-valine or proline (or the protected derivatives thereof) as starting materials and using (2R,3S)-3-amino-4-methyl-1,1,1-trifluoro-2-pentanol at the appropriate coupling steps.

Substantially or essentially pure SSS diastereoisomer may be obtained, for example, by oxidation of (S)-1-[(S)-2-(methoxycarbonylamino)-3-methylbutyryl]-N-[(S)-2-methyl-1-((R)-2,2,2-trifluoro-1-hydroxyethyl)propyl] pyrrolidine-2-carboxamide (of formula IIa) with a suitable oxidising agent, such as one of the oxidising agents referred to above. The starting alcohol may be obtained as shown in Scheme 2.

Crystalline forms of the SSS diastereoisomer containing 35% or less of the SSR diastereoisomer may be obtained from a non-crystalline (amorphous) diastereomeric mixture of the SSS and SSR diasteroisomers, containing the SSS and SSR diastereoisomers in approximately equal amounts (i.e. a ratio of about 1:1, typically 53:47 or 47:53) by crystallisation from a suitable non-polar solvent, such as a mixture of methyl tert-butyl ether and hexane, preferably containing a small quantity of water and optionally containing a small amount of hydrochloric acid, for example 0–0.2 mole equivalents of 36% w/w hydrochloric acid and 1–2.1 mole eqivalents of water. It is found preferable to add aqueous hydrochloric acid to the solvent of crystallisation when a non-crystalline diastereomeric mixture of SSS:SSI rato of 47:53 is used. To initiate crystallisation, seeding with crystalline SSS diastereoisomer is preferred. The crystalline product is generally isolated as a mixture of hydrated and ketone form, typically in a ratio of about 80:20 (hydrated:ketone) or greater. A hydrated form or a mixture of ketone and hydrated forms may be converted to the substantially or essentially "ketone" form by drying in a vacuum oven (for example at about 50° C.). However, such a ketone form is hygroscopic.

Substantially or essentially pure crystalline forms of the SSS diastereoisomer may be obtained by recrystallisation or repeated recrystallisation of crystalline forms of the SSS diasteroisomer containing SSR diastereoisomer. Solvents or mixtures of solvents which may be used include, for example, butyl acetate, butyl acetate/hexane, acetone/water, acetone/hexane, acetone/petroleum fraction b.p. 100–120° C., 1,2-dimethoxyethane/hexane, 1,2-dimethoxyethane/water/hexane, ethyl acetate/water/hexane, ethyl acetate/hexane, water, dibutylether/hexane, dichloromethane/hexane, 1,2-dimethoxyethane/water, methanol/toluene, methyl tert-butyl ether/hexane, isopropanol/hexane and tetrahydrofuran/hexane. To obtain Form A, the first ten solvents or mixtures of solvents referred to above are preferred. Wet ethyl acetate/hexane is particularly useful to obtain Form A. Particularly useful solvents or mixtures of solvents to obtain Form B are 1,2-dimethoxyethane/water and water/methanol, although this form may also be obtained when ethyl acetate/water/hexane is used. Where hexane is referred to herein, this includes isomers of hexane (such as iso-hexane) or mixtures thereof.

Substantially or essentially pure crystalline forms of the SSS diastereoisomer may also be obtained by crystallisation of substantially or essentially pure SSS diastereoisomer isolated in a non-crystalline form (for example by oxidation of the compound of formula IIa), such as an oil, using similar solvents or mixtures of solvents referred to above, especially a mixture of ethyl acetate, water and hexane.

Furthermore, Form A may also be obtained from Form B by recrystallisation, for example as illustrated in Example 9. In addition the crystalline "ketone" form (which is hygroscopic) may be obtained from Form A, for example, as illustrated in Example 10.

The preparation of a ketal or hemi-ketal from a ketone is well known in the art.

3-Amino-4-methyl-1,1,1-trifluoro-2-pentanol may be obtained as described in U.S. Pat. No. 4.910,190 or as illustrated in the Examples.

A particularly advantageous procedure for the manufacture of (2R,3S)-3-amino-4-methyl-1,1,1-trifluoro-2-pentanol, which is a further aspect of the present invention, comprises (as illustrated in Scheme 3): (1) reaction of (2RS,3SR)-3-amino-4-methyl-1,1,1-trifluoro-2-pentanol, or a salt thereof, with triphosgene or dimethyl carbonate in the presence of a suitable base to give (4RS,5SR)-4-isopropyl-5-trifluoromethyloxazolidin-2-one; followed by (2) reaction of (4RS,5SR)-4-isopropyl-5-trifluoromethyloxazolidin-2-one, or an alkali metal salt thereof, with (−)-menthyl chloroformate to give (4RS,5SR)-4-isopropyl-3-[(1R,3R,4S)-3-p-menthyloxycarbonyl]-5-trifluoromethyloxazolidin-2-one and separation of the (4S,5R)-4-isopropyl-3-[(1R,3R,4S)-3-pmenthyloxycarbonyl]-5-trifluoromethyloxazolidin-2-one isomer; followed by (3) hydrolysis of (4S,5R)-4-isopropyl-3-[1R,3R,4S)-3-p-menthyloxycarbonyl]-5-trifluoromethyloxazolidin-2-one isomer under basic conditions, to give (2R,3S)-3-amino-4-methyl-1,1,1-trifluoro-2-pentanol.

In Step (1), a suitable base is an aqueous alkali metal hydroxide, for example sodium or potassium hydroxide. The reaction is generally carried out in a suitable inert solvent or diluent, for example a hydrocarbon such as toluene. The reaction is exothermic and so the reaction is generally carried with external cooling maintaining the temperature at about 0° C. to 50° C., for example at about ambient temperature.

In step (2), the reaction is carried out in a suitable solvent or diluent, for example an ethereal solvent such as tetrahydrofuran. Conveniently the oxazolidinone is converted to its alkali metal salt, for example using butyllithium at about −78° C., prior to addition of the (−)-menthyl chloroformate. On work-up, the desired (4S,5R)-isomer crystallises from the mixture of isomers and is collected by filtration.

In step (3), suitable conditions include, for example, the use of an aqueous solution of an alkali metal hydroxide (such as sodium or potassium hydroxide) in an ethereal solvent or diluent, such as dioxan, at a temperature in the range of, for example, 60–130° C. (such as 90–120° C.).

The utility of the compound of the invention may be demonstrated by standard tests and clinical studies, including those described below.

Inhibition Measurements:

The potency of the compound of the invention (or a particular form thereof) to act as an inhibitor of human leukocyte elastase (HLE) on the low molecular weight peptide substrate methoxy-succinyl-alanyl-alanyl-prolyl-valine-p-nitroanilide is determined as described in U.S. Pat. No. 4,910,190. The potency of the compound is evaluated by obtaining a kinetic determination of the dissociation constant, $K_i$, of the complex formed from the interaction of the inhibitor with HLE. The compound of Example 1 was found to have a $K_i$ of 36 nM. The compound of Example 2 was found to have a $K_i$ of 9 nM.

Acute Lung Injury Model:

Animal models of emphysema include intratracheal (i.t.) administration of an elastolytic protease to cause a slowly progressive, destructive lesion of the lung. These lesions are normally evaluated a few weeks to a few months after the initial insult. However, these proteases also induce a lesion that is evident in the first few hours. The early lesion is first hemorrhagic, progresses to an inflammatory lesion by the end of the first 24 hours and resolves in the first week post insult. To take advantage of this early lesion, the following model may be used.

Hamsters are first lightly anesthetized with Brevital. Phosphate buffered saline (PBS) pH 7.4, either alone or containing human leukocyte elastase (HLE), is then administered directly into the trachea. Twenty-four hours later the animals are killed and the lungs removed and carefully trimmed of extraneous tissue. Following determination of wet lung weight, the lungs are lavaged with PBS and total lavagable red and white cells recovered are determined. The values for wet lung weights, total lavagable red cells and total lavagable white cells are elevated in a dose-dependent manner following administration of HLE. Compounds that are effective elastase inhibitors can prevent or diminish the severity of the enzyme-induced lesion resulting in lower wet lung weight and reduced values for total lavagable cells, both red and white, relative to administration of HLE alone. Compounds can be evaluated by administering them intratracheally as solutions or suspensions in PBS, either with or at various times prior to the HLE challenge (400 $\mu$g), or by dosing them intravenously or orally as solutions at various times prior to the HLE challenge (100 $\mu$g) to determine their utility in preventing an HLE lesion. A solution of the compound of the invention (or a particular form thereof) may be conveniently prepared using 10% polyethylene glycol 400/PBS.

Acute Hemorrhagic Assay:

This assay relies on monitoring only the amount of hemorrhage in the lung following intratracheal administration of human neutrophil elastase (HNE). Hemorrhage is quantified by disrupting erythrocytes recovered in lung lavage fluid and comparing that to dilutions of whole hamster blood. The screening protocol, similar to that described in Fletcher et-al., *American Review of Respiratory Disease* (1990), 141, 672–677, is as follows. Compounds demonstrated to be HNE inhibitors in vitro are conveniently prepared for dosing as described above for the Acute Lung Injury Model. Male Syrian hamsters (fasted for 16–18 hours prior to use) are lightly anaesthetised with Brevital sodium (30 mg/kg i.p.). The compounds are then dosed intravenously or orally to the hamsters at a fixed time, such as 30 or 90 min, prior to intratracheal administration of 50 $\mu$g/animal of HNE in 300 $\mu$L phosphate buffered saline (PBS) pH 7.4. Four hours after enzyme administration, the animals are killed with an overdose of pentobarbital sodium, the thorax opened and the lungs and heart removed and the lungs cleared of extraneous material. The excised lungs are lavaged with three changes of 2 ml PBS via a tracheal cannula. The recovered lavages are pooled, the volumes (about 5 mL) are recorded and the lavages stored at 4° C. until assayed. For calculation of the amount of blood in each sample, the thawed lavages and a sample of whole hamster blood are sonicated to disrupt erythrocytes and appropriately diluted into individual wells of a 96-well microtiter plate. The optical densities (OD) of the disrupted lavages and blood samples are determined at 540 nm. The ($\mu$L blood equivalents)/(mL lavage) are determined by comparing the OD of the test samples with the OD of the standard curve prepared from whole hamster blood. The total $\mu$L equivalents of blood recovered is determined by multiplying recovered lavage volume by the ($\mu$L blood equivalents)/(mL lavage) for each sample. Results are reported as % inhibition of HNE-induced hemorrhage with respect to PBS treated controls when the test compound is given at a specified dose and time prior to administration of HNE. The $ED_{50}$ for the compound of Example 1 was found to be 4.5 mg/kg after oral dosing. The $ED_{50}$ for the compound of Example 2 was found to be 1.9 mg/kg after oral dosing and 0.6 mg/kg after i.v. administration.

No overt toxicity was observed when the compound of the invention was administered in the above in vivo tests.

It will be appreciated that the implications of a compound's activity in the Acute Lung Injury Model or Acute Hemorrhagic Assay are not limited to emphysema, but, rather, that the test provides evidence of general in vivo inhibition of HLE.

According to a further feature of the invention, there is provided a pharmaceutical composition comprising a pharmaceutically effective amount of the compound of the invention (or a particular form thereof), or a solvate thereof, and a pharmaceutically acceptable diluent or carrier. As noted above, another feature of the invention is a method of using the compound of the invention (or a particular form thereof), or a solvate thereof, in the treatment of a disease or condition in a mammal, especially a human, in which HLE is implicated, such as those referred to hereinbefore, and particularly acute and chronic bronchitis, pulmonary emphysema, reperfusion injury, adult respiratory distress syndrome, cystic fibrosis, or peripheral vascular disease (such as critical limb ischaemia or intermittent claudication).

The compound of the present invention (or a particular form thereof) may be administered to a warm-blooded animal, particularly a human, in need thereof for treatment of a disease in which HLE is implicated, in the form of a conventional pharmaceutical composition, for example as generally disclosed in U.S. Pat. No. 4,910,190. One mode of administration may be via a powdered or liquid aerosol. In a powdered aerosol, the compound of the invention (or a particular form thereof) may be administered in the same manner as cromolyn sodium via a 'Spinhaler' (a trademark) turbo-inhaler device obtained from Fisons Corp. of Bedford, Mass. at a rate of about 0.1 to 50 mg per capsule, 1 to 8 capsules being administered daily for an average human. Each capsule to be used in the turbo-inhaler contains the required amount of the compound of the invention (or the particular form thereof) with the remainder of the 20 mg capsule being a pharmaceutically acceptable carrier such as lactose. In a liquid aerosol, the compound of the invention (or a particular form thereof) may be administered using a nebulizer such as, for example, a 'Retec' (trademark) nebulizer, in which the solution is nebulized with compressed air. The aerosol may be administered, for example, at the rate of one to about eight times per day as follows: A nebulizer is filled with a solution of the compound (or a particular form thereof), for example 3.5 mL of solution containing 10 mg/mL; the solution in the nebulizer is nebulized with compressed air; and the patient breathes normally (tidal volume) for eight minutes with the nebulizer in his mouth.

Alternatively, the mode of administration may be parenteral, including subcutaneous deposit by means of an osmotic pump or, preferably, oral. The compound of the invention (or a particular form thereof) may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice, e.g. as described in U.S. Pat. No. 3,755,340. For parenteral administration, a 1 to 10 mL intravenous, intramuscular or subcutaneous injection would be given containing about 0.02 mg to 10 mg/kg of body weight of the compound of the invention (or a particular form thereof) 3 or 4 times daily. The injection would contain the compound of the invention (or a particular form thereof) in an aqueous isotonic sterile solution or suspension optionally with a preservative such as phenol or a solubilizing agent such as ethylenediaminetetraacetic acid (EDTA). For parenteral administration or use in an aerosol, an aqueous formulation may be prepared, for example, by dissolving the compound (or a particular form thereof) in 5–10% polyethylene glycol 400/phosphate buffered saline, followed by aseptic filtration, and sterile storage using standard procedures.

In general, the compound of the invention (or a particular form thereof) will be administered to humans at a daily dose in the range of, for example, 5 to 100 mg of the compound (or a particular form thereof) by aerosol or 50 to 1000 mg intravenously or orally, or a combination thereof. However, it readily will be understood that it may be necessary to vary the dose of the compound (or a particular form thereof) administered in accordance with well known medical practice to take account of the nature and severity of the disease under treatment, concurrent therapy, and the age, weight and sex of the patient receiving treatment. It similarly will be understood that generally equivalent amounts of a solvated (for example, hydrated) form of the compound also may be used. Protocols for the administration of an HLE inhibitor and evaluation of the patients are described in the European Patent Applications with Publication Numbers 458535, 458536, 458537, and 463811 for the treatment or prevention of cystic fibrosis, ARDS, bronchitis, and hemorrhage associated with acute non-lymphocytic leukemia or its therapy, respectively; and the compound of the invention (or a particular form thereof) may be used similarly, or preferably used by oral administration, for the treatment of those diseases and conditions either alone or in combination with another therapeutic agent customarily indicated for the treatment of the particular condition. For therapeutic or prophylactic treatment of a vascular disease or related condition in a mammal in which neutrophils are involved or implicated, a compound of the invention (or a particular form thereof) may conveniently be administered by an oral or parenteral route, either alone or simultaneously or sequentially with other therapeutically active agents customarily administered for the condition. The utility of the compound of the invention (or a particuler form thereof) in such treatment of vascular diseases and related conditions may be demonstrated using the procedures described in International Patent Application, Publication No. WO 92/22309.

The various aspects of the invention will now be illustrated by the following non-limiting examples in which, unless stated otherwise:

(i) temperatures are given in degrees Celsius (° C.); operations were carried out at room or ambient temperature, that is, at a temperature in the range of 18–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means 'flash chromatography' (method of Still) carried out on Merck Kieselgel (Art 9385 from E. Merck, Darmstadt, Germany), elution using both step and ramp gradients is denoted by the parenthetical term "gradient" followed by the initial and final solvent ratios; thin layer chomatography (TLC) was carried out on silica plates, for example 0.25 mm silica gel GHLF plates (Art 21521 from Analtech, Newark, Del., USA);

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory nuclear magnetic resonance (NMR) spectra; and, where examined, were substantially pure by HPLC;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (THS) as an internal standard, determined at 250 MHz using DMSO-$d_6$ as solvent; conventional abbreviations for signal shape are used; for AB spectra the directly observed shifts are reported;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms;

(xii) mass spectra (MS) were run with an electron energy of 70 electron volts in the chemical ionizaton mode using a direct exposure probe; where indicated ionization was effected by electron impact (EI) or fast atom bombardment (FAB); generally, only peaks which indicate the parent mass are reported; and (xiii) HPLC was used to establish the ratio of SSS:SSR diastereoisomers of formula I in isolated material, using a SUPELCO LC-18 reversed-phase, 25cm×4.6 mm column and water:acetonitrile (70:30) as eluant. The flow rate was 1.0 ml/min, the injection volume was 20 μl by valve and the detection wavelength was 205 nm. The retention time for the SSS diastereisomer was about 9.9 minutes and that for the SSR diastereoisomer was about 11.7 minutes.

EXAMPLE 1

1-(3-Dimethylaminopropyl)-3-ethylcarbodiimide hydrochloride (1.84 g) was added to a solution of (S)-1-[(S)-2-(methoxycarbonylamino)-3-methylbutyryl]-N-[2-methyl-1-(2,2,2-trifluoro-1-hydroxyethyl)propyl]pyrrolidine-2-carboxamide (0.41 g) dissolved in dimethylsulphoxide (DMSO; 5 ml) and toluene (5 ml), followed by dropwise addition of dichloroacetic acid (0.32 ml). The resulting solution was allowed to stir at 20° C. for 2 hours. The solution was then poured into ethyl acetate (200 ml) and washed successively with 1M hydrochloric acid, water and brine. The organic solution was dried (MgSO$_4$) and concentrated under vacuum. The residue was purified by flash chromatography (gradient elution; methanol:methylene chloride, 3:97 to 5:95) to give (S)-1-[(S)-2-(methoxycarbonylamino)-3-methylbutyryl]-N-[2-methyl-1-(2,2,2-trifluoroacetyl)propyl]pyrrolidine-2-carboxamide (0.27 g) as a white foam (as a mixture of ketone and hydrated forms); TLC, R$_f$=0.4 (methanol:dichloromethane, 2.5:97.5); $^1$H NMR (DMSO/D$_2$O): 4.44 (m, 1H), 4.00 (m, 2H), 3.72 (m, 1H), 3.51 (m, 4H), 202–1.75 (m, 6H), 0.95–0.78 (m, 12H); Analysis for C$_{18}$H$_{28}$F$_3$N$_3$O$_5$.0.3H$_2$O: Calculated: C, 50.42; H, 6.72; N, 9.80; Found: C, 50.31; H, 6.28; N, 9.56.

The starting material (S)-1-[(S)-2-(methoxycarbonylamino)-3-methylbutyryl]-N-[2-methyl-1-(2,2,2-trifluoro-1-hydroxyethyl)propyl]-pyrrolidine-2-carboxamide was obtained as follows:

Methyl chloroformate (0.12 ml) was added to a solution of (2RS,3SR)-L-valyl-N-[3-(4-methyl-1,1,1-trifluoro-2-hydroxypentyl)]-L-prolinamide (obtained as described in U.S. Pat. No. 5,194,588) (0.5 g) and triethylamine (0.57 ml) in dichloromethane (13.6 ml) at 0° C. The solution was allowed to stir for 0.5 hours, and then poured into ethyl acetate (100 ml). The organic solution was washed successively with saturated aqueous sodium bicarbonate solution, water and brine. The solution was dried (MgSO$_4$) and concentrated under vacuum. The residue was purified by flash chromatography (gradient elution; methanol:methylene chloride, 5:95 to 7:93) to give (S)-1-[(S)-2-(methoxycarbonylamino)-3-methylbutyryl]-N-[2-methyl-1-( 2,2,2-trifluoro-1-hydroxyethyl)propyl]pyrrolidine-2-carboxamide (0.51 g); TLC, R$_f$=0.2 (methanol:methylene chloride, 5:95); MS: m/z=426(M+1).

EXAMPLE 2

A solution of potassium permanganate (16.6 g) in water (100 ml) was added dropwise to a 0° C. solution of (S)-1-[(S)-2-(methoxycarbonylamino)-3-methylbutyryl]-N-[(S)-2-methyl-1-((R)-2,2,2-trifluoro-1-hydroxyethyl)propyl] pyrrolidine-2-carboxamide (15 g) in tert-butyl alcohol (175 ml), water (100 ml), and 0.6 M sodium hydroxide solution (175 ml). The solution was stirred for 2 hours and then quenched by addition of methanol (70 ml), followed by stirring for 1 hour. The mixture was filtered through diatomaceous earth and the filtrate made acidic to pH 2 using 1M hydrochloric acid, and saturated with sodium chloride. The product was extracted into ether (5×100 ml) and the solvent removed under vacuum. The resulting oil was chromatographed (methanol: dichloromethane 5:95) and the solvent removed to give an oil. Hexane (40 ml) was added to a stirred solution of the oil in ethyl acetate (which had been presaturated with water) (40 ml) and stirring was continued for 24 hours over which time a crystalline solid formed. Another portion of hexane (40 ml) was added and the solid was collected and dried under vacuum (40° C.) to give (S)-1-[(S)-2-(methoxycarbonylamino)-3-methylbutyryl]-N-[(S)-2-methyl-1-(2,2,2-trifluoroacetyl)propyl]-pyrrolidine-2-carboxamide (9.45 g) as a white crystalline solid (as substantially or essentially Form A); $^1$H NMR (300 MHz, DHSO/D$_2$O): 4.42 (m, 1H) 4.02 (d, 1H), 3.73 (m, 1H), 3.59 (m, 1H), 3.54 (s, 3H), 2.23 (m, 1H), 2.00–1.76 (m, 6H), 0.91 (m, 6H), 0.85 (d, 3H), 0.80 (d, 3H); Analysis for C$_{18}$H$_{28}$F$_3$N$_3$O$_5$.H$_2$O: Calculated; C, 48.97; H, 6.85; N, 9.51; Found: C, 49.02, H, 6.80; N, 9.66; AXDS shown in FIG. 1). The starting material (S)-1-[(S)-2-(methoxycarbonylamino)-3-methylbutyryl]-N-[(S)-2-methyl-1-((R)-2,2,2-trifluoro-1-hydroxyethyl)propyl] pyrrolidine-2-carboxamide was obtained as follows:

(i) N-[(Phenylmethoxy)carbonyl]-L-valyl-L-proline tert-butyl ester (905 g) was dissolved in ethanol (4 liters) and 10% palladium on carbon (20 g) was added. The reaction mixture was shaken under a hydrogen atmosphere (50 psi) for 12 hours and then the catalyst was removed by filtration through through diatomaceous earth. The filtrate was concentrated under vacuum and the residue twice re-evaporated from toluene (1 liter) to give L-Valyl-L-Proline tert-butyl ester as an oil (628 g); TLC, R$_f$=0.2, acetone:hexane (20:80); MS: m/z=271(M+1).

(ii) A solution of sodium carbonate (110.5 g) in water (1.5 liters) and L-Valyl-L-Proline tert-butyl ester in tetrahydrofuran (THF; 1 liter) were combined and cooled to 0° C. The mixture was diluted with ether (400 ml) and methyl chloroformate (39.4 g) was added dropwise. The reaction mixture was then allowed to warm ambient temperature over 2 hours. The layers were separated and the organic phase was washed twice with 1M hydrochloric acid, followed by saturated aqueous sodium bicarbonate solution and brine. The aqueous phase was extracted with ether. All organic phases were combined and dried (MgSO$_4$) and the solvent removed to give N-(methoxycarbonyl)-L-valyl-L-proline tert-butyl ester (125.9 g); $^1$H NMR (300 MHz, DMSO/d4-trifluoroacetic acid): 4.23 (dd, 1H), 4.06 (d, 1H), 3.78 (m, 1H), 3.57 (m, 1H), 3.55 (s, 3H), 2.16 (m, 1H), 1.95 (m, 3H), 1.80 (m, 1H), 1.42 (s, 9H), 0.94 (m, 6H); MS: m/z=329 (M+1).

(iii) To a solution of N-[methoxycarbonyl]-L-valyl-L-proline tert-butyl ester (813 g) in toluene (3 liters) was added Amberlyst-15 ion exchange resin (190 g). The reaction was heated at 120° C. to distill off water present in the resin via a water/toluene azeotrope. Approximately 400 ml of distillate was collected. Heating was then continued at reflux for 1.5 hours. The reaction was cooled to 60° C. and the resin was removed by filtration. The filtrate was extracted with 1M NaOH (2.5 liters) followed by saturated aqueous sodium bicarbonate solution. The combined basic extracts were extracted with a mixture of THF/ethyl acetate (1:1, 1 liter), and then cooled in an ice bath. The aqueous solution was made acidic to pH 1.5 using cold 3M hydrocloric acid (1 liter) and extracted twice with THF/ethyl acetate (1:1, 1.5 liters and 1 liter). The extracts were combined and washed with brine, dried (MgSO$_4$), and the solvent removed by evaporation. The resulting material was dissolved in ether (1 liter) and allowed to crystallize at 0° C. over 48 hours. The resulting solid was collected by filtration, washed with cold ether and dried under vacuum to give N-[methoxycarbonyl]-L-valyl-L-proline (373 g); $^1$H NMR (300 MHz, DMSO) 12.4 (s, 1H), 7.37 (d, 1H), 4.25 (dd, 1H), 4.00 (t, 1H), 3.79 (m, 1H), 3.55 (m, 1H), 3.51 (s, 3H), 2.11 (m, 1H), 1.85 (m, 4H), 0.91 (d, 3H), 0.87 (d, 3H); MS m/z=273 (H+1).

(iv) N-Methylmorpholine (8.5 ml) was added to a solution of N-(methoxycarbonyl)-L-valyl-L-proline (12.5 g) in THF (150 ml) and the solution was cooled to −15° C. in an ice/acetone bath. Isobutyl chloroformate (6.6 ml) was added dropwise and the mixture was stirred for 1 hour. A second portion of N-methylmorpholine (8.5 ml) was added, followed by (2R,3S)-3-amino-4-methyl-1,1,1-trifluoro-2-pentanol hemioxalate salt (10 g). The reaction mixture was then allowed to stir for 12 hours while allowing to warm to ambient temperature. The reaction mixture was diluted with ether (500 ml) and washed successively with saturated aqueous sodium bicarbonate solution, 1M HCl and brine. The aqueous layers were extracted with ether and all organic phases were combined and dried (MgSO$_4$). The solution was filtered and the solvent removed by evaporation. The resulting material was filtered through silica gel using ether as the eluant. The ether fractions containing the product were combined and the solvent removed by evaporation. The product was dried under vacuum to give (S)-1-[(S)-2-(methoxycarbonylamino)-3-methylbutyryl]-N-[(S)-2-methyl-1-(R)-(2,2,2-trifluoro-1-hydroxyethyl)propyl]-pyrrolidine-2-carboxamide (16.1 g); $^1$H NMR (300 MHz, DMSO): 7.61 (d, 1H), 7.28 (d, 1H), 6.44 (d, 1H), 4.44 (m, 1H),–4.05 (m, 1H), 3.98 (m, 1H), 3.75 (m, 2H), 3.55 (m, 1H), 3.50 (s, 3H), 1.83 (m, 6H), 0.90 (d, 3H), 0.86 (d, 3H); MS: m/z=426.

(2R,3S)-3-amino-4-methyl-1,1,1-trifluoro-2-pentanol hemioxalate salt, used in step (iv), was obtained as follows:

(i) Triphosgene (23 g) was added in one portion to a well stirred mixture of (2RS,3SR)-3-amino-4-methyl-1,1,1-trifluoro-2-pentanol hemioxalate salt (50 g) in toluene (250 ml) and 2M sodium hydroxide solution (350 ml). The reaction began to exotherm and was placed in an ice bath. After 0.5 hour the reaction was warmed to 25° C. and TLC indicated a substantial amount of unreacted amine present. The pH of the solution was readjusted to about 12 using 50% sodium hydroxide solution. An additional portion of triphosgene (8 g) was added and the solution was stirred for 1 hour. The pH of the reaction mixture was lowered to pH 7 using 1H hydrochloric acid and extracted twice with ether. The combined ether layers were washed with water, brine and dried (MgSO$_4$). The solvent was removed by evaporation to give an oil, which crystallized upon standing. The resulting solid was collected by filtration and washed with ether:hexane (1:1) to give 27 g of (4RS),5SR)-4-isopropyl-5-trifluoromethyloxazolidin-2-one as a white solid, m.p. 71–72° C.; $^1$H NMR (300 MHz, DMSO): 8.45 (s, 1H), 5.11 (m, 1H), 3.61 (m, 1H), 1.72 (m, 1H), 0.86 (d, 6H).

(ii) n-Butyllithium (20 ml of a 10M solution in hexane) was added to a solution of (4RS,5SR)-4-isopropyl-5-trifluoromethyl-oxazolidin-2-one (35.8 g) in THF (600 ml) at −78° C., followed by stirring for 0.5 hours. (−)-Henthyl chloroformate (41 ml, freshly distilled) was added followed by continuation of stirring at −78° C. for 0.5 hours. The solution was warmed to 25° C. and the reaction quenched by addition of saturated aqueous sodium bicarbonate solution. The product was extracted into ether and washed with water and brine. The solution was dried (MgSO$_4$) and the solvent removed under vacuum. The resulting oil crystallized upon standing to give a solid which was collected by filtration. The solid was washed with ether:hexane (1:1) and dried to give (4S,5R)-4-isopropyl-3-[(1R,3R,4S)-3-p-menthyloxycarbonyl]-5-trifluoromethyloxazolidine-2-one (23.15 g); m.p. 138–140° C.; $^1$H NMR (300 MHz, DMSO): 5.51 (dd, 1H), 4.68 (m, 1H), 4.26 (m, 1H), 2.27 (m, 1H), 1.94 (d, 1H), 1.78 (m, 1H), 1.62 (d, 2H), 1.42 (m, 2H), 1.01 (dd, 2H), 0.95–0.84 (m, 24H), 0.71 (d, 3H); $^{19}$FNMR (376.5 HHz,DMS0): −76.9910; 99% d.e. (A further crop of 4.3 g (99% d.e.) was obtained from the mother liquor). [Note: the (4R,5S) isomer has m.p. 80–82° C. and 19FNMR (376.5 MHz, DHSO): −77.0019.

(iii) A solution of (4S,5R)-4-isopropyl-3-[(1R,3R,4S)-3-p-menthyloxycarbonyl]-5-trifluoromethyloxazolidin-2-one (27 g) in dioxane (70 ml) and 50% potassium hydroxide solution (80 ml) was heated at 100° C. for 2 days. The reaction was cooled, diluted with ether (400 ml) and the organic layer separated. The PH of the aqueous solution was adjusted to 9 (originally about 14) using 6M hydrochloric acid. The aqueous layer was extracted 3 times with ether (300 ml). The organic phases were combined, dried (MgSO$_4$), and added to a well stirred solution of oxalic acid dihydrate (4.5 g) in acetonitrile (100 ml). The solid which precipitated was collected by filtration, washed with ether, and dried under vacuum (60° C.) to give 15.9 g of white solid. The solid was triturated with ether (300 ml), collected by filtration and dried to give (2R,3S)-3-amino-4-methyl-1,1,1-trifluoro-2-pentanol isolated as its hemioxalate salt (13.4 g, 88% yield) as a white solid, m.p. 184–186° C.; $^1$H NMR (300 MHz, DMSO): 5.71 (bs, 3H), 4.08 (ddd, 1H), 2.88 (m, 1H), 1.81 (m, 1H), 0.92 (m, 6H); Analysis for $C_6H_{12}F_3N0.0.5C_2H_2O_4$: C, 38.89; H, 6.06; N, 6.48; Found: C, 38.75; H, 5.95; N, 6.47.

(2RS,3SR)-3-Amino-4-methyl-1,1,1-trifluoro-2-pentanol used in step (i) was obtained as described in U.S. Pat. No. 4,910,190.

EXAMPLE 3

Using a similar oxidation procedure to that described in Example 2, but using (S)-1-[(S)-2-(methoxycarbonylamino)-3-methylbutyryl]-N-[2-methyl-1-(2,2,2-trifluoro-1-hydroxyethyl)propyl]-pyrrolidine-2-carboxamide and adding the potassium permanganate solution at 5–10° C. and then stirring at 10° C. for one hour prior to treatment with methanol, there was obtained (after work-up by extraction into tert-butyl methyl ether, followed by washing with brine and concentration in vacuo) (S)-1-[(S)-2-(methoxycarbonylamino)-3-methylbutyryl]-N-[2-methyl-1-(2,2,2-trifluoroacetyl)propyl]-pyrrolidine-2-carboxamide as a gum (in 75% yield); SSS:SSR ratio of 53:47; hydrate:ketone 1:1; $^1$H NMR similar to that of the product of Example 1. [Using a similar procedure, but adding the potassium permanganate solution at ambient temperature instead of 5–10° C., the product was obtained in a ratio of SSS:SSR of 47:53.]

The starting material (S)-1-[(S)-2-(methoxycarbonylamino)-3-methylbutyryl]-N-[2-methyl-1-(2,2,2-trifluoro-1-hydroxyethyl)-propyl]pyrrolidine-2-carboxamide was obtained as an oil (in 55% yield) using an analogous procedure to that described in Example 2, part (iv), but using 3-amino-4-methyl-1,1,1-trifluoro-2-pentanol (as a mixture of diastereoisomers), itself obtained as described in U.S. Pat. No. 4,910,190 or as follows:

(i) A solution of urea (72 g) in DMF (810 ml) was added to sodium nitrite (90 g), stirred for 10 minutes and then cooled to 15° C. Isobutyl iodide (97.2 ml) was added over 30 minutes and the reaction mixture allowed to stir at ambient temperature for 20 hours. The mixture was re-cooled to 15° C. and water (810 ml) was added slowly. The mixture was was stirred for 5 minutes at ambient temperature and then extracted twice with methyl tert-butyl ether. The combined organic extracts were washed twice with 20% aqueous sodium thiosulphate solution and concentrated under vacuum to give 2-methyl-1-nitropropane (39 g), which was used without further purification.

(ii) 3A Molecular sieves (27.04 g) were heated at 120° C. under vacuum for 20 hours and added to a solution of 2-methyl-1-nitropropane (13.0 g) in methyl tert-butyl ether (420 ml). The mixture was stirred for 5 minutes, potassium carbonate (64.5 g) added and the mixture stirred a further 30 minutes. The mixture was cooled to 15° C. and fluoral hydrate (22.0 g) was added over 30 minutes. The reaction mixture was stirred at ambient temperature for 16 hours, then cooled to 15° C. and water (270 ml) added. After stirring for 5 minutes at ambient temperature, the organic phase was separated and washed with 10% aqueous potassium carbonate, 2M hydrochloric acid solution and water. Solvent was then removed by evaporation under reduced pressure at a temperature below 40° C. and the oil azeotroped dry with isopropyl alcohol at a temperature below 50° C. to give 4-methyl-3-nitro-1,1,1-trifluoro-2-pentanol (21.3 g) as an oil, which was used without further purification.

(iii) A solution of 4-methyl-3-nitro-1,1,1-trifluoro-2-pentanol (17.1 g) in isopropanol (115 ml) and acetic acid (0.43 ml) was hydrogenated over 10% palladium on carbon (2.4 g) at 3.5 bar pressure until uptake of hydrogen was complete. The catalyst was removed by filtration through diatomaceous earth and the filter cake washed with isopropanol. The filtrate was evaporated under vacuum until no further isopropanol distilled and the residue dissolved in acetonitrile (40 ml). A solution of oxalic acid (3.94 g) in acetonitrile (80 ml) was added with stirring and the mixture cooled to 5° C. The product which crystallised was collected by filtration, washed with cold acetonitrile and dried at 50° C. to give 3-amino-4-methyl-1,1,1-trifluoro-2-pentanol as its oxalate salt (9.08 g).

EXAMPLE 4

Hexane (13 ml) was added to a solution of (S)-1-[(S)-2-(methoxycarbonylamino)-3-methylbutyryl]-N-[2-methyl-1-(2,2,2-trifluoroacetyl)propyl]pyrrolidine-2-carboxamide (0.85 g; SSS:SSR 53:47; hydrate:ketone 1:1) in tert-butyl methyl ether (8.5 ml) until cloudiness persisted. The solution was then warmed to give a clear solution, seeded with substantially pure crystalline SSS diastereoisomer and allowed to stand. A white solid crystallised which was collected by filtration to give (S)-1-[(S)-2-(methoxycarbonylamino)-3-methylbutyryl]-N-I(S)-2-methyl-1-(2,2,2-trifluoroacetyl)propyl]-pyrrolidine-2-carboxamide as a crystalline solid in 30% yield, SSS:SSR 95:5; hydrate:ketone 80:20; NMR similar to that of the product of Example 2.

EXAMPLE 5

Using a similar procedure to that described in Example 4, but starting with a diastereomeric mixture of SSS:SSR 53:47 (1.73 g) and hydrate:ketone 95:5, but adding 36% w/w hydrochloric acid (0.06 ml) and water (0.04 ml) to the crystallisation solvent prior to the addition of the hexane, crystalline SSS diastereisomer was obtained in 22% yield with SSS:SSR 98.5:1.5 and substantially or essentially in a hydrate form.

EXAMPLE 6

Using a similar procedure to that described in Example 5, but excluding the hydrochloric acid, a crystalline diastereomeric mixture was obtained with SSS:SSR 65:35 and substantially or essentially in a hydrate form.

EXAMPLE 7

Using a similar procedure to that described in Example 5, but starting with a diastereomeric mixture of SSS:SSR 47:53 and hydrate:ketone 60:40, crystalline SSS diastereoisomer was obtained in 18% yield with SSS:SSR 98.5:1.5 and substantially or essentially in a hydrate form.

EXAMPLE 8

The product of Example 2 (5 g) was dissolved in 1,2-dimethoxyethane (DME; 6 ml) with slight warming. Water (5 ml) was carefully added to the solution to give a clear solution. The solution was allowed to cool to ambient temperature, seeded with substantially pure crystalline SSS diastereoisomer and allowed to stand for 16 hours. The crystalline mass which had formed in the bottom of the vessel was carefully broken up and collected by vacuum filtration. The crystalline product was washed with a mixture of DME and water and allowed to dry in a current of air for 16 hours to give crystalline SSS diastereoisomer (containing less then 2% SSR diastereoisomer) as substantially or essentially Form B, with a water content of 7.3% w/w; (XDS spectrum shown in FIG. 3). [Using a similar procedure but using recrystallised Form A as starting material, Form B was obtained having a water content of 7.7% w/w.]

EXAMPLE 9

The product of Example 8 (4.78 g) was dissolved in ethyl acetate (14.7 ml) with warming to 60° C. under an inert atmosphere. Hexane (22 ml) was added slowly and the solution was allowed to cool to 22° C. The crystalline product was collected by filtration and washed with hexane (10 ml), then allowed to dry in a current of air to give crystalline SSS diastereoisomer (containing less then 2% SSR diastereoisomer) as substantially or essentially Form A, with a water content of 4.1% w/w.

EXAMPLE 10

The product of Example 2 (1 g) was dissolved in cyclohexane (20 ml) and the solution was distilled at atmospheric pressure at 80° C. to reduce the volume to 7 ml. The clear solution was then allowed to cool to 24° C. The suspended solid was collected by suction filtration carried out under a current of dry nitrogen and dried in a desiccator under vaccum in the presence of phosphorus pentoxide. There was thus obtained crystalline SSS diastereoisomer (containing less then 2% SSR diastereoisomer) in substantially or essentially the "ketone" form; (XDS spectrum shown in FIG. 4).

Chemical Formulae

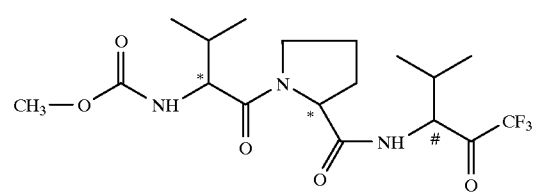

I

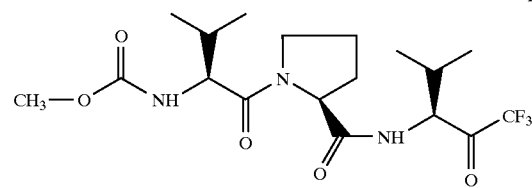

Ia

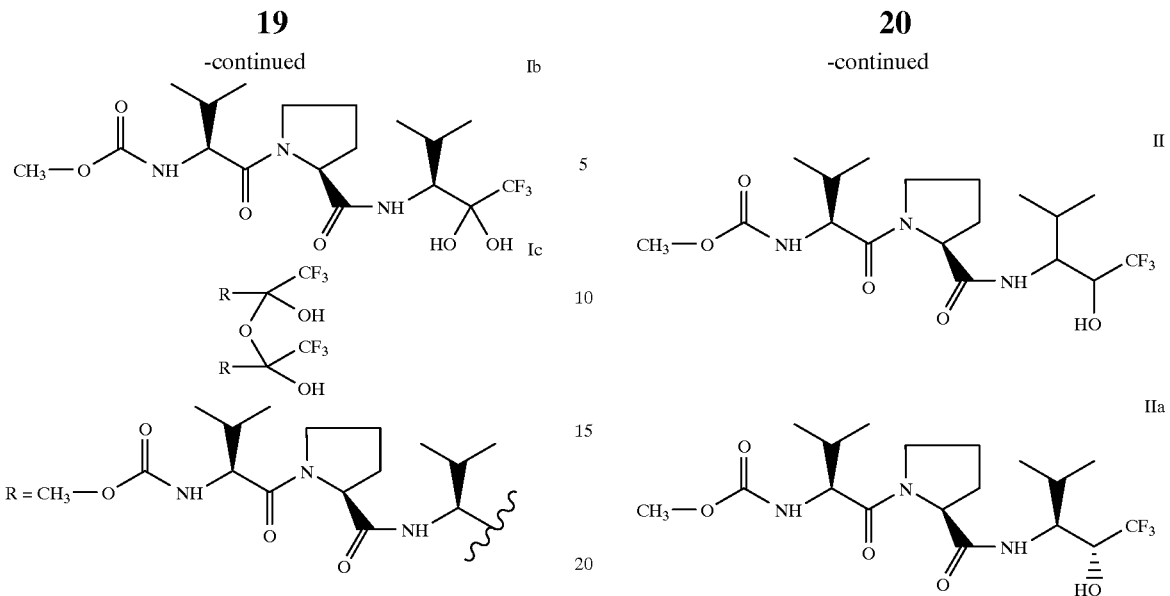
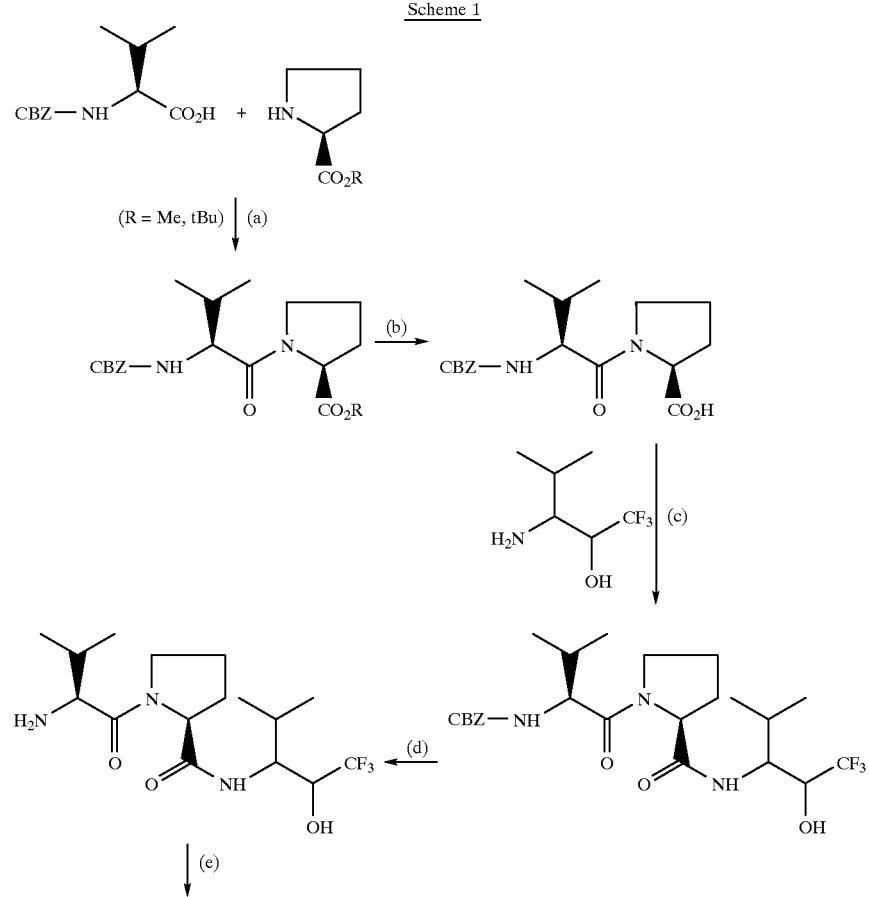

-continued

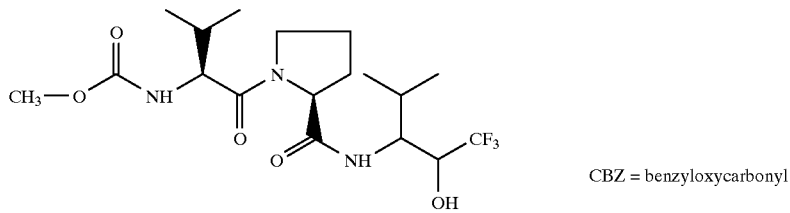

CBZ = benzyloxycarbonyl

Suitable conditions include:

(a) DMF, 1-hydroxybenztriazole, Et$_3$N, dicyclohexylcarbodiimide, 0° C. to ambient temperature
(b) R = $^t$Bu: trifluoroacetic acid, CH$_2$Cl$_2$, 0° C. to ambient temperature
R = Me: methanol/aqueous NaOH, ambient temperature
(c) $^i$BuO•CO•Cl, N-methylmorpholine, THF, -35° C. to 0° C., followed by the aminoalcohol
(d) H$_2$, 10% Pd-C, EtOH
(e) CH$_3$O•CO•Cl, Et$_3$N, CH$_2$Cl$_2$, 0° C.

Scheme 2

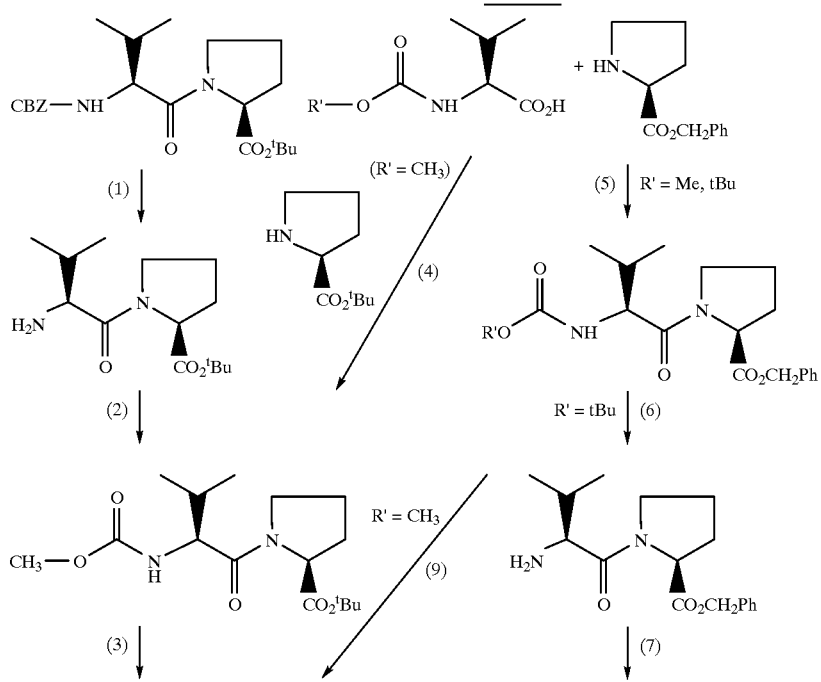

-continued
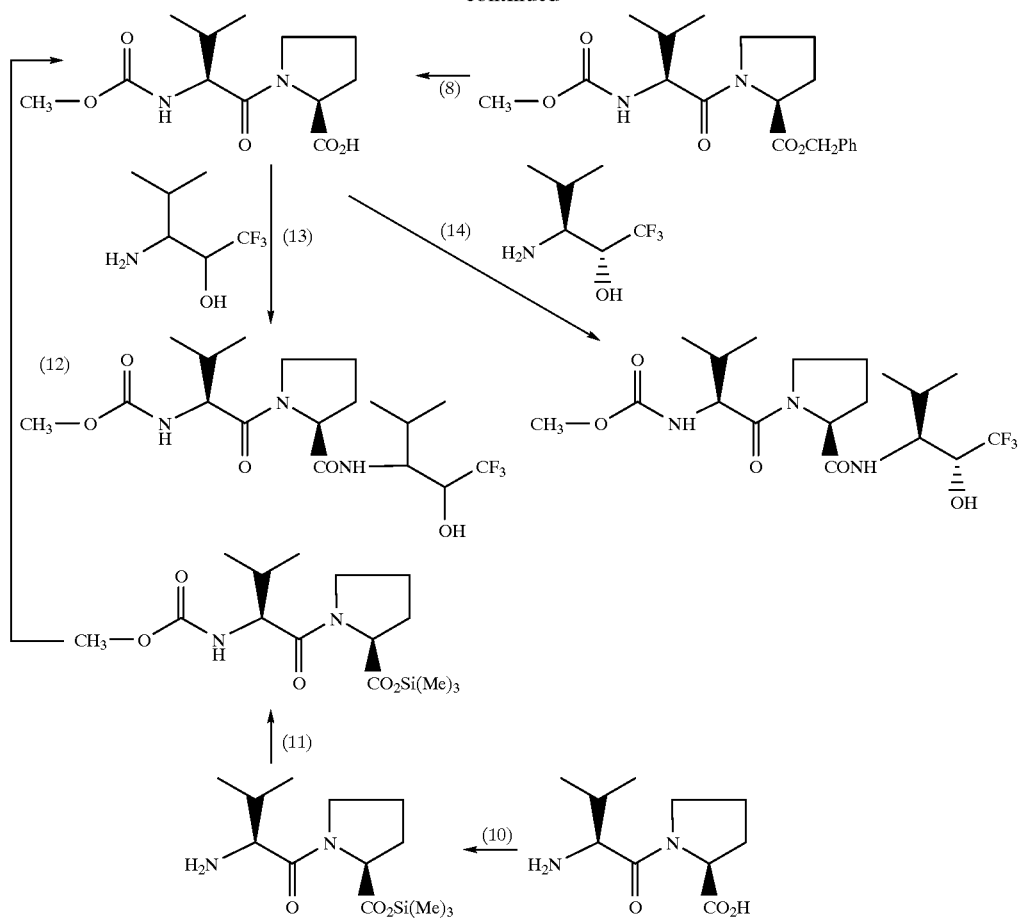
Suitable conditions for Scheme 2 include:
Steps (1), (8), (9): as for Step (d) of Scheme 1; Steps (2), (7),
(11): MeOCOCl, Et$_3$N or N-methylmorpholine, CH$_2$Cl$_2$ or THF, 0° C. to 30° C.;
Steps (3), (6): trifluoroacetic acid, CH$_2$Cl$_2$, 0° C. to ambient temp;
Steps (4), (5): as for Step (a) of Scheme 1; Step (10): Me$_3$SiCl, THF, N-methylmorpholine, 0–30° C.; Step (12): acidic aqueous hydrolysis;
Steps (13), (14): as for step (c) of Scheme 1
Scheme 3
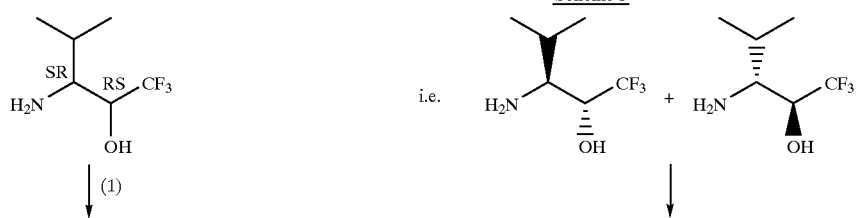

-continued

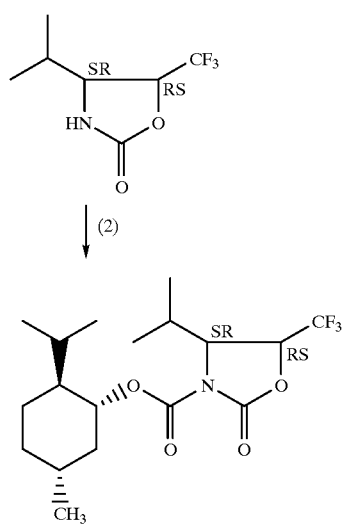

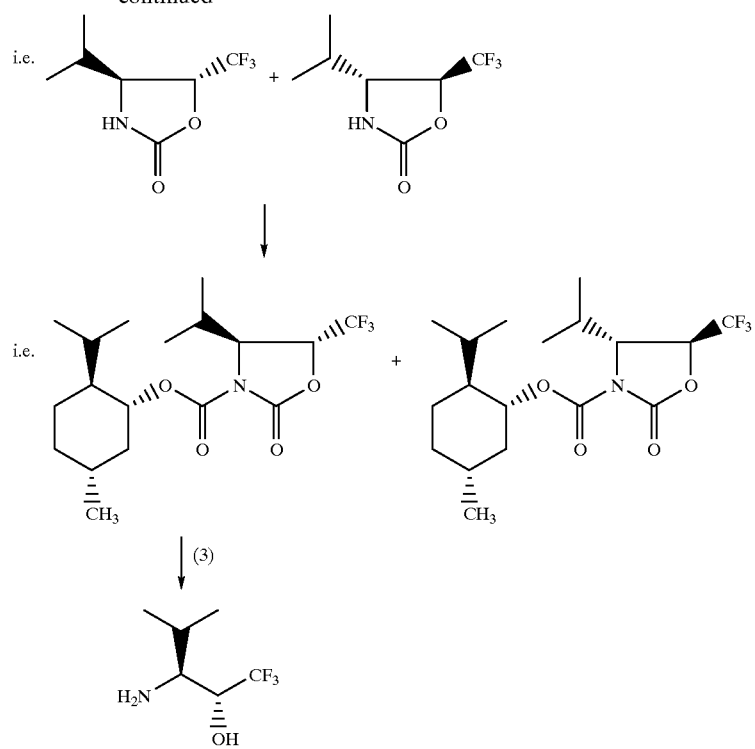

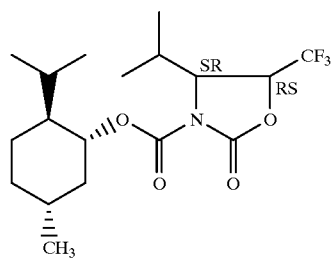

What is claimed is:

1. A compound of the formula II or IIa

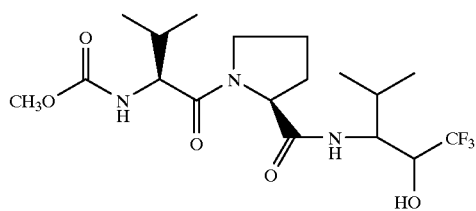

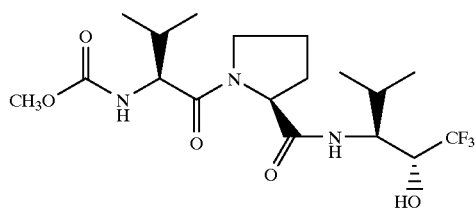

2. A compound obtained by the process of (a) oxidizing a compound of formula IIa

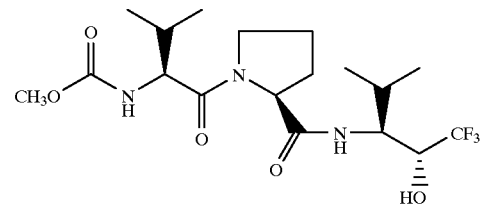

with a suitable oxidizing agent; and (b) forming crystals from a solution of the product formed in step (a) in a solvent selected from butyl acetate, a mixture of butyl acetate and hexane, a mixture of acetone and water, a mixture of acetone and hexane, a mixture of acetone and petroleum ether b.p. 100–120° C., a mixture of 1,2-diemthoxyethane and hexane, a mixture of 1,2-diemthoxyethane, water and hexane, a mixture of ethyl acetate and hexane, a mixture of ethyl acetate, hexane and water, water, a mixture of dibutyl ether and hexane, a mixture of dichloromethane and hexane, a mixture of methanol and toluene, a mixture of tert-butyl methyl ether and hexane, a mixture of isopropanol and hexane and a mixture of tetrahydrofuran and hexane.

* * * * *